US008728049B2

(12) United States Patent
Hammons et al.

(10) Patent No.: US 8,728,049 B2
(45) Date of Patent: *May 20, 2014

(54) ABSORBENT ARTICLE HAVING A TUFTED TOPSHEET

(75) Inventors: John Lee Hammons, Hamilton, OH (US); Sybille Fuchs, Frankfurt (DE); Luisa Valerio Gonzalez, Oakley, OH (US)

(73) Assignee: The Procter & Gamble Company, Cincinnati, OH (US)

(*) Notice: Subject to any disclaimer, the term of this patent is extended or adjusted under 35 U.S.C. 154(b) by 453 days.

This patent is subject to a terminal disclaimer.

(21) Appl. No.: 12/415,150

(22) Filed: Mar. 31, 2009

(65) Prior Publication Data

US 2010/0036347 A1 Feb. 11, 2010

Related U.S. Application Data

(63) Continuation-in-part of application No. 12/188,543, filed on Aug. 8, 2008, now Pat. No. 7,967,801, and a continuation-in-part of application No. 12/188,598, filed on Aug. 8, 2008, now Pat. No. 8,058,501.

(51) Int. Cl.
*A61F 13/15* (2006.01)
*A61F 13/20* (2006.01)

(52) U.S. Cl.
USPC ............... 604/385.101; 604/367; 604/385.01; 604/382

(58) Field of Classification Search
USPC ................ 604/385.01, 367, 378, 382–383, 604/385.101
See application file for complete search history.

(56) References Cited

U.S. PATENT DOCUMENTS

| 5,180,620 A | 1/1993 | Mende |
| 5,792,404 A | 8/1998 | Cree |
| 5,795,345 A | 8/1998 | Mizutani |
| 5,873,869 A | 2/1999 | Hammons et al. |
| 6,287,288 B1 * | 9/2001 | Osborn et al. ........... 604/385.04 |

(Continued)

FOREIGN PATENT DOCUMENTS

| FR | 2 713 083 | 6/1995 |
| JP | 2005/177086 | 7/2005 |
| JP | 2007/037660 | 2/2011 |
| WO | 2004/058118 | * 7/2004 ............ A61F 13/15 |

OTHER PUBLICATIONS

PCT International Search Report dated Oct. 28, 2009.
U.S. Appl. No. 12/188,493, filed Aug. 8, 2008, Hammons et al.

(Continued)

*Primary Examiner* — Michele M Kidwell
(74) *Attorney, Agent, or Firm* — Andrew J. Hagerty

(57) ABSTRACT

An absorbent article having a topsheet and an absorbent core. The topsheet has a pair of tuft region lateral boundaries. Each tuft region lateral boundary is defined by a line or a portion of a line separating a plurality of the tufts from a portion of the topsheet devoid of tufts. Tuft region lateral boundaries are symmetrically disposed on opposing sides of the longitudinal centerline. Tuft region lateral boundaries extend longitudinally along at least part of the longitudinal centerline. Tuft region lateral boundaries are spaced apart from each other by a distance gradually increasing from a minimum at a parallel transverse axis to a maximum at longitudinally opposing ends of the tuft region lateral boundaries or are spaced apart from each other by a distance gradually decreasing from a maximum at a parallel transverse axis to a minimum at longitudinally opposing ends of the tuft region lateral boundaries.

13 Claims, 13 Drawing Sheets

(56) References Cited

U.S. PATENT DOCUMENTS

| | | |
|---|---|---|
| 6,383,431 B1 | 5/2002 | Dobrin |
| 6,733,610 B2 | 5/2004 | Mizutani et al. |
| 6,911,574 B1 | 6/2005 | Mizutani |
| 7,172,801 B2 | 2/2007 | Hoying et al. |
| 7,410,683 B2 | 8/2008 | Curro et al. |
| 7,507,459 B2 | 3/2009 | Turner et al. |
| 7,553,532 B2 | 6/2009 | Turner et al. |
| 7,579,062 B2 * | 8/2009 | Cabell .............................. 428/97 |
| 7,754,050 B2 * | 7/2010 | Redd et al. .................... 162/125 |
| 8,030,535 B2 | 10/2011 | Hammons et al. |
| 2004/0229008 A1 | 11/2004 | Hoying |
| 2005/0119631 A1 | 6/2005 | Giloh et al. |
| 2005/0281976 A1 | 12/2005 | Curro et al. |
| 2006/0286343 A1 | 12/2006 | Curro et al. |
| 2007/0116926 A1 | 5/2007 | Hoying et al. |
| 2007/0219522 A1 | 9/2007 | Mishima et al. |
| 2008/0119807 A1 | 5/2008 | Curro et al. |
| 2008/0154226 A9 | 6/2008 | Hammons |
| 2008/0300564 A1 * | 12/2008 | Bogren et al. ................ 604/367 |
| 2009/0030390 A1 | 1/2009 | Hammons et al. |
| 2009/0030391 A1 | 1/2009 | Hammons |
| 2009/0157030 A1 | 6/2009 | Turner et al. |

OTHER PUBLICATIONS

U.S. Appl. No. 12/188,527, filed Aug. 8, 2008, Hammons et al.
U.S. Appl. No. 12/188,543, filed Aug. 8, 2008, Hammons et al.
U.S. Appl. No. 12/188,598, filed Aug. 8, 2008, Hammons et al.
U.S. Appl. No. 12/470,945, filed May 22, 2009, Turner et al.

* cited by examiner

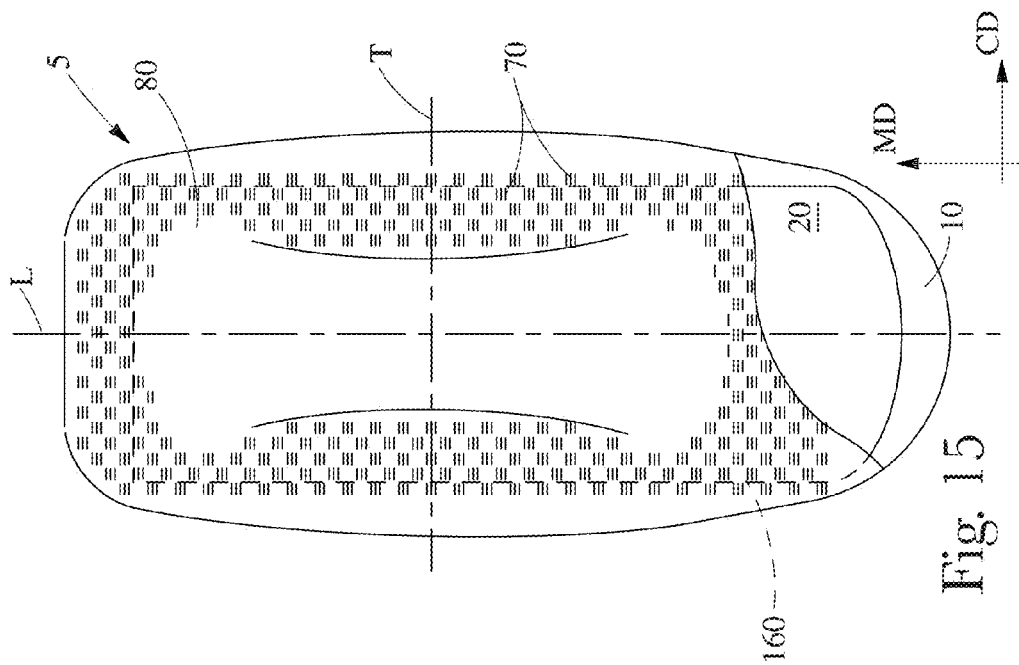
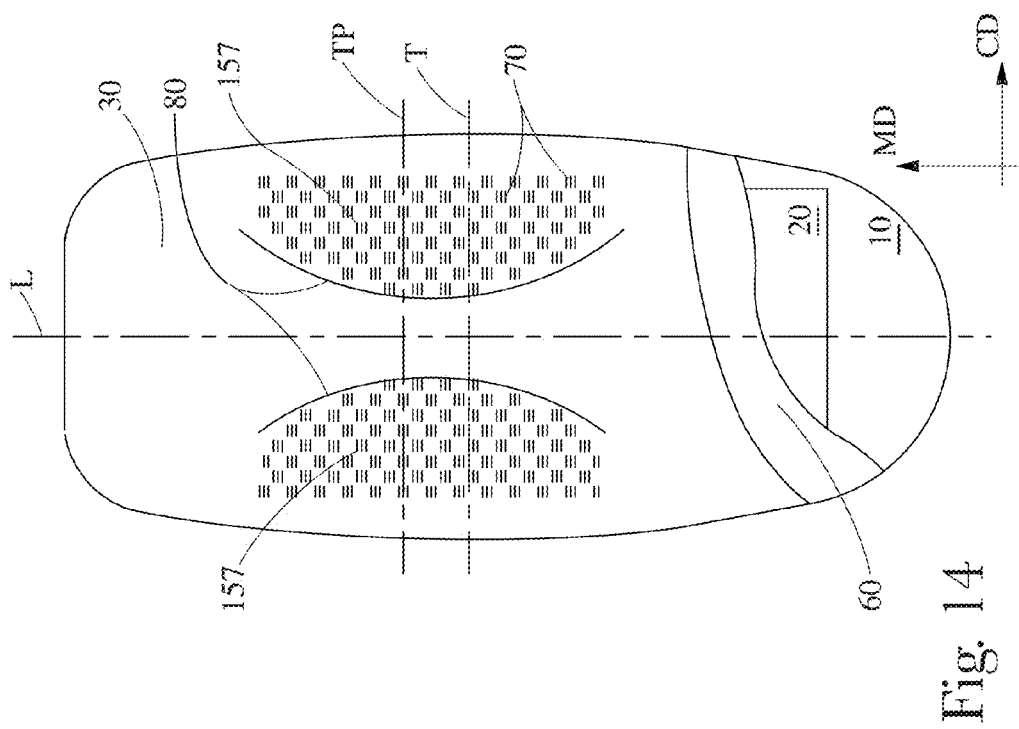

ABSORBENT ARTICLE HAVING A TUFTED TOPSHEET

CROSS REFERENCE TO RELATED APPLICATION

This application is a continuation-in-part of application Ser. No. 12/188,543, filed Aug. 8, 2008 now U.S. Pat. No. 7,967,801. This application is a continuation-in-part of application Ser. No. 12/188,598, filed Aug. 8, 2008.

FIELD OF THE INVENTION

An absorbent article having a tufted topsheet.

BACKGROUND OF THE INVENTION

Absorbent articles such as disposable diapers, incontinence products, catamenial products, and the like are widely used and much effort has been expended to improve the effectiveness and functionality of these articles. In general such articles have a fluid pervious topsheet, a backsheet, and an absorbent core between the topsheet and backsheet.

Conventional topsheets used in absorbent articles typically exhibit a tradeoff between fluid acquisition/retention performance of the topsheet and comfort of the topsheet against the wearer's skin. When worn, different portions of absorbent articles might be designed deliver different benefits. For instance, in the center portion of an absorbent article, a topsheet having a high fluid acquisition rate might be desirable. Further, in the center portion of an absorbent article, a topsheet having limited rewet might be desirable so that the wearer does not feel a sticky sensation against her labia. For portions other than the center portion of an absorbent article, a surface texture that is soft and supple might be desirable so as to reduce chafing that might occur as the wearer moves and the peripheral parts of an absorbent article rub against the wearer's body.

When worn, absorbent articles generally conform to the three-dimensional shape of the wearer's body. In the crotch region of a woman, there are a variety of curved features. For instance, where the legs join the trunk of the person in the crotch, there are portions where there are curved boundaries between the legs and the trunk. The labial region of a woman's crotch also tends to be defined by a region having curved boundaries. For absorbent articles such as sanitary napkins designed to be worn in the crotch region of a woman to capture fluid discharged from her vagina, the absorbent article can be attached to the woman's panty and flaps attached to the absorbent article might be wrapped about edges of the crotch region of the woman's panty. The leg openings of the crotch region of common panties tend to be curved and the body facing surface of absorbent articles generally conform to this curve when worn.

Commonly available absorbent articles tend to have topsheets in which the surface of the topsheet is generally uniform. The reasons for this include that less expensive materials can be used as the topsheet and manufacturing costs can tend to be lower.

Accordingly, there is a continuing unaddressed need for absorbent articles having a topsheet in which different portions of the topsheet have different characteristics that provide different benefits in different portions of the topsheet.

SUMMARY OF THE INVENTION

An absorbent article comprising a topsheet and an absorbent core in facing relationship with the topsheet. The topsheet has a longitudinal centerline, a transverse centerline orthogonal to and intersecting the longitudinal centerline, and a parallel transverse axis parallel to the transverse centerline. The longitudinal centerline is dividable into thirds. One third of the longitudinal centerline is a middle third. The parallel transverse axis intersects the middle third of the longitudinal centerline. The topsheet comprises a fibrous nonwoven web and tufts. The tufts comprise fibers integral with and extending from the fibrous nonwoven web. A plurality of the fibers of the tufts are looped fibers. The topsheet comprises a pair of tuft region lateral boundaries symmetrically disposed on opposing sides of the longitudinal centerline. Each tuft region lateral boundary is defined by a line or a portion of a line extending along at least part of the longitudinal centerline and separating a plurality of the tufts from a portion of the topsheet devoid of tufts. The tuft region lateral boundaries are spaced apart from each other by a distance gradually increasing from a minimum at the parallel transverse axis to a maximum at one or both longitudinally opposing ends of the tuft region lateral boundaries or are spaced apart from each other by a distance gradually decreasing from a maximum at the parallel transverse axis to a minimum at one or both longitudinally opposing ends of the tuft region lateral boundaries.

BRIEF DESCRIPTION OF THE DRAWINGS

FIG. 14 is a schematic top view of an absorbent article in which the tufts have a first color and the portion of the topsheet devoid of tufts has a second color.

FIG. 15 is a schematic of a top cutaway view of an absorbent article.

DETAILED DESCRIPTION OF THE INVENTION

Figure 1:
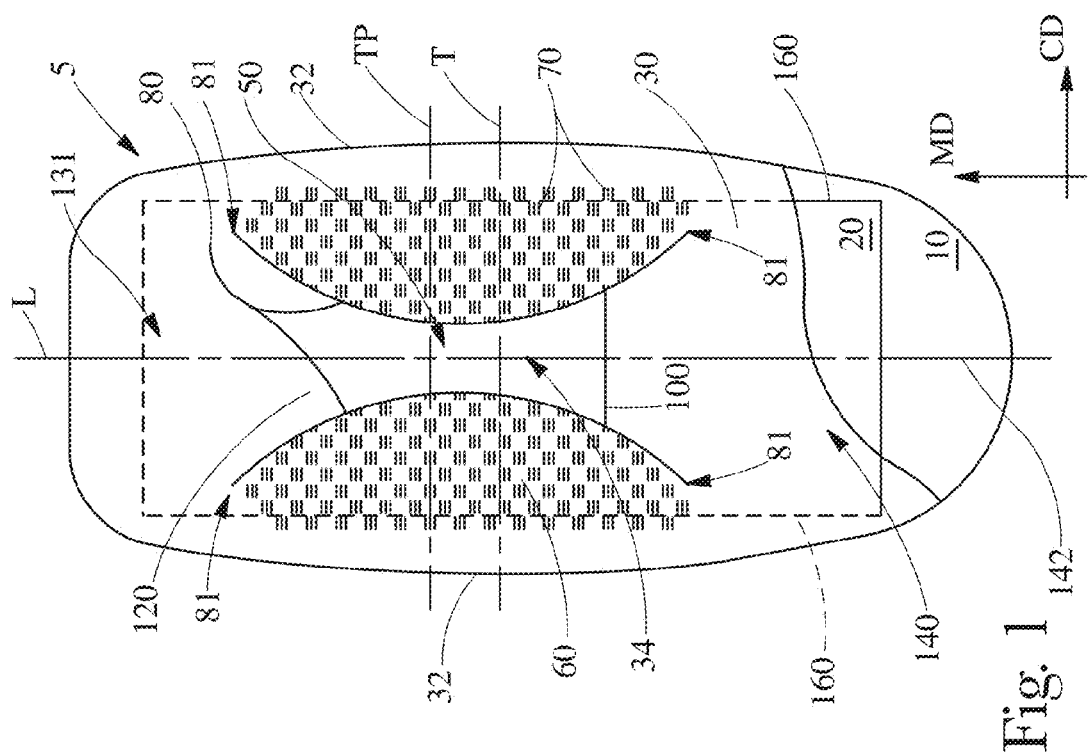
FIG. 1 is a schematic of a top cutaway view of an absorbent article.

FIG. 1 is an illustration of a partial cutaway view of an absorbent article 5 comprising a topsheet 30, a backsheet 10, and an absorbent core 20 disposed between the topsheet 30 and backsheet 10. The topsheet 30 is in facing relationship with the absorbent core 20. The topsheet 30 and absorbent core can be considered to be in facing relationship if one surface of the topsheet is oriented towards the absorbent core 20. The topsheet 30 can be in facing relationship with the absorbent core 20 even if an additional layer or layers of material are between the topsheet 30 and the absorbent core 20. The absorbent core 20 can be described as being in fluid communication with the topsheet 30. That is fluid can be transmitted from the topsheet 30 to the absorbent core 20 directly or through an intermediate layer or layers between the topsheet 30 and absorbent core 20. For example, the topsheet 30 and absorbent core 20 can be in facing relationship such that one side of the topsheet 30 faces the absorbent core 20. The topsheet 30 is referred to herein as a generally planar, two-dimensional web, the length and width of which are substantially greater than the thickness of the web. The absorbent core 20 can be the absorbent core employed in ALWAYS Ultra or INFINITY sanitary napkins, manufactured by The Procter & Gamble Co. The absorbent core can be Foley Fluff pulp available from Buckeye Technologies Inc., Memphis, Tenn. that is disintegrated and formed into a core having a density of about 0.07 grams per cubic centimeter (g/cm$^3$) and a caliper of less than about 10 mm.

The topsheet 30 has a longitudinal centerline L. For absorbent articles 5 that are symmetric about the longest dimension of the absorbent article, the longitudinal centerline L can divide the absorbent article into halves and can be a longest dimension of the absorbent article 5. For instance, for an absorbent article 5 worn in the crotch region of the wearer, the longitudinal centerline L can divide the absorbent article 5 into left and right halves, left and right being taken from the viewpoint of the wearer properly wearing the absorbent article 5. The topsheet 30 has a transverse centerline T that is orthogonal to the longitudinal centerline L and bisects the longitudinal centerline L. The longitudinal centerline L and transverse centerline T define a two-dimensional plane of the topsheet 30 prior to use, which in the embodiment shown is associated with the machine direction MD and the cross machine direction CD, as is commonly known in the art of making absorbent articles 5 on high speed production lines.

The topsheet 30 can have a parallel transverse axis TP that is parallel to the transverse centerline T. The longitudinal centerline L can be divided into thirds, i.e. three parts of equal length with length being measured along the longitudinal centerline L, the front third 131, the middle third 50, and the rear third 140. The front third 131 is the portion of the topsheet 30 that is generally oriented towards the wearer's pubic area when the absorbent article 5 is worn. The rear third 140 is the portion of the topsheet 30 that is generally oriented towards the wearer's anus when the absorbent article 5 is worn. The middle third 50 is the portion of the topsheet 30 that is generally aligned with the crotch area between the wearer's legs proximal to the vagina. The front third 131 and rear third 140 are at longitudinally disposed ends of the absorbent article 5 and the middle third 50 is between the front third 131 and rear third 140. The parallel transverse axis TP intersects the longitudinal centerline L in the middle third 50 of the absorbent article 5. The longitudinal centerline L has a length 142 defined by the dimension of the topsheet 30 measured along the longitudinal centerline.

The absorbent article 5 has a body facing surface 120 that is the face of the absorbent article 5 that is oriented towards the wearer when the absorbent article 5 is in use.

The topsheet 30 can comprise a fibrous nonwoven web 60 and tufts 70. The topsheet can further comprise a pair of tuft region lateral boundaries 80. The tuft region lateral boundaries 80 can be symmetrically disposed on opposing sides of the longitudinal centerline L. The tuft region lateral boundaries 80 have longitudinally opposing ends 81. Each tuft region lateral boundary 80 can be defined by a line or portion of a line separating a plurality of the tufts 70 from a portion of the topsheet 30 that is devoid of the tufts 70. A line can be considered to be a straight or curved geometric feature that is generated by moving a point and that has extension only along the path of the point. The absorbent core 20 can be between the fibrous nonwoven web 60 from which the tufts 70 extend and the backsheet 10. The absorbent core 20 can have a pair of core lateral edges 160 spaced away from the longitudinal centerline L.

The tuft region lateral boundaries 80 are illustrated herein as lines for clarity, the lines representing the boundary between the different portions of topsheet 30. Actual lines (e.g. printed lines, pigmented lines etc.) need not appear on the topsheet 30 to demarcate the tuft region lateral boundaries 80. Rather, the tuft region lateral boundary 80 can be the location at which there is a contrast between a part of the fibrous nonwoven web 60 having tufts 70 and a part of fibrous nonwoven web 60 that is devoid of the tufts 70.

As shown in FIG. 1, the tuft region lateral boundaries 80 can be symmetrically disposed on opposing sides of the longitudinal centerline L. That is, the tuft region lateral boundaries 80 can be mirror images of one another with respect to the longitudinal centerline L. The tuft region lateral boundaries 80 can extend along at least part of the longitudinal centerline L (e.g. at more than one location on the longitudinal centerline L a straight line originating from the longitudinal centerline L and orthogonal to the longitudinal centerline L will intersect a tuft region lateral boundary 80) on transversely opposite sides of the longitudinal centerline L of the topsheet 30. Thus, when the body facing surface 120 of the absorbent article 5 is viewed, the tuft region lateral boundaries 80 can divide the topsheet 30 into at least three distinct parts, two of which are spaced apart towards the absorbent article lateral side edges 32 of the absorbent article 5 and one of which is the central part 34 of the topsheet 30 that is generally coincidental with the longitudinal centerline L.

The central part 34 of the topsheet 30 can function primarily as a fluid collecting component and the parts of the topsheet spaced apart towards the lateral side edges 32 can function to provide for skin comfort and/or as a barrier to fluid runoff.

The tuft region lateral boundaries 80 can be spaced apart from each other by a distance 100 that is gradually increasing from a minimum at the parallel transverse axis TP to a maximum at one or both of the longitudinally opposing ends 81 of the tuft region lateral boundaries 80. The distance 100 can gradually increase as a function of location along the longitudinal centerline L such that portions of the tuft region lateral boundaries 80 are straight or curved. The ends of the tuft region lateral boundaries 80 need not necessarily be free ends beyond which the topsheet 30 is devoid of tufts.

One or more of the tuft region lateral boundaries 80 can extend along at least part of the length 142 of the longitudinal centerline L such that the tuft region lateral boundary 80 is longer than one-fourth of the length 142 of the topsheet 30, the length of a tuft region lateral boundary 80 being measured along the tuft region lateral boundary 80. The tuft region lateral boundary 80 can be longer than one-third of the length 142 of the topsheet 30. The tuft region lateral boundary 80 can be longer than one-half of the length 142 of the topsheet 30.

Figure 2:
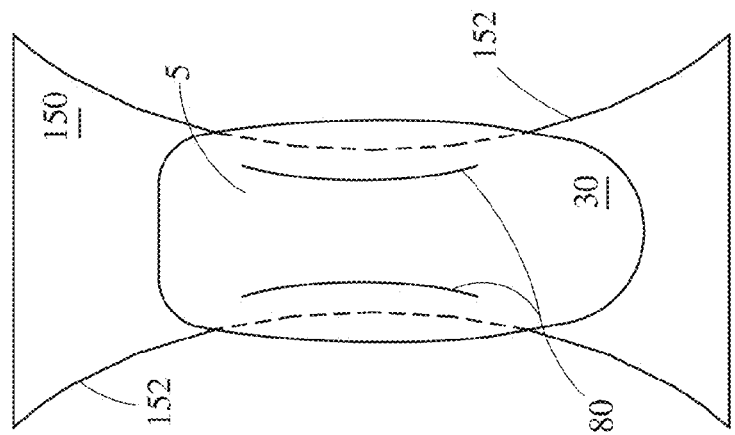
FIG. 2 is a schematic of an absorbent article placed in a panty.

Tuft region lateral boundaries 80 that are spaced apart from each other by a distance 100 that is gradually increasing from a minimum at the parallel transverse axis TP to a maximum at longitudinally opposing ends of the tuft region lateral boundaries 80 are thought to possibly provide a number of benefits. FIG. 2 is an illustration of an absorbent article 5 placed in the crotch region of a wearer's panty 150. Fuller coverage panties

150, as opposed to thong style, tend to have curved leg openings 152. The curved leg openings 152 tend to fit proximal where the wearer's legs intersect her crotch. When an absorbent article 5 is worn in the panty 150, the absorbent article 5 can tend to coincide with the crotch of the panty 150 or extend laterally slightly beyond the curved leg openings 152. Tuft region lateral boundaries 80 that are spaced apart from each other by a distance 100 that is gradually increasing from a minimum at the parallel transverse axis TP to a maximum at longitudinally opposing ends 81 of the tuft region lateral boundaries 80 can tend to coincide with the natural contours of the woman's crotch where her legs join her crotch. Soft and supple tufts 70 having tufts 70 formed from a soft and supple fibrous nonwoven web 60 on the topsheet 30 laterally beyond the tuft region lateral boundaries 80, that is, away from longitudinal centerline L, can make the absorbent article 5 more comfortable to wear as the woman moves. The part of the topsheet 30 between the tuft region lateral boundary 80 and the longitudinal centerline L can be devoid of the tufts 70. The part of the topsheet 30 between the tuft region lateral boundary 80 and the longitudinal centerline L can comprise other structural features to provide for improved fluid acquisition and fluid retention, such as apertures.

The tuft region lateral boundaries 80 can extend along more than about 35% of length of the longitudinal centerline L. The tuft region lateral boundaries 80 can extend along between about 35% and about 85% of the length of the length of the longitudinal centerline L. The tuft region lateral boundaries 80 can extend along between about 40% and about 60% of the length of the longitudinal centerline L. Without being bound by theory, it is thought that tuft region lateral boundaries 80 can have a length that is roughly the same or larger than the length of the typical wearer's labial region or length of the intersection between her leg and her crotch and be practical. The tuft region lateral boundaries 80 can extend along more than about 50 mm of the length of the longitudinal centerline L.

The distance 100 between tuft region lateral boundaries 80 can be a minimum of about 10 mm at the parallel transverse axis TP. The distance 100 can be a maximum of about 120 mm.

Tufts 70 can also aid with fluid acquisition, provide for some separation between the wearer's body and the topsheet 30, and provide for improved rewet characteristics. Having tufts 70 located in the portion of the topsheet between (i.e. laterally inward) of the tuft region boundaries 80, that is towards the longitudinal centerline L of the topsheet 30, can provide for such characteristics to be proximal the wearer's labia and vagina where such characteristics might provide for the most fruitful benefit rather than out towards the lateral side edges where fluid acquisition and retention may not be of great concern. That is, part of the topsheet 30 between a tuft region lateral boundary 80 and the longitudinal centerline can comprise tufts 70. Tufts 70 can provide for improved fluid acquisition because the fibers of the tufts 70 converge at the base of the tufts, thereby forming small capillaries having high suction to drive fluid flow. The looped fibers 110 of the tuft 70 can provide for separation between the wearer's body and the topsheet 30 by structurally acting as arches of fibers 110 that resist compression, which also can reduce rewet upon compression. Tufts can be a plurality of raised loops of fibers or a pile of fibers integral with and out of plane of the web from which the loops or pile extend.

Figure 3:
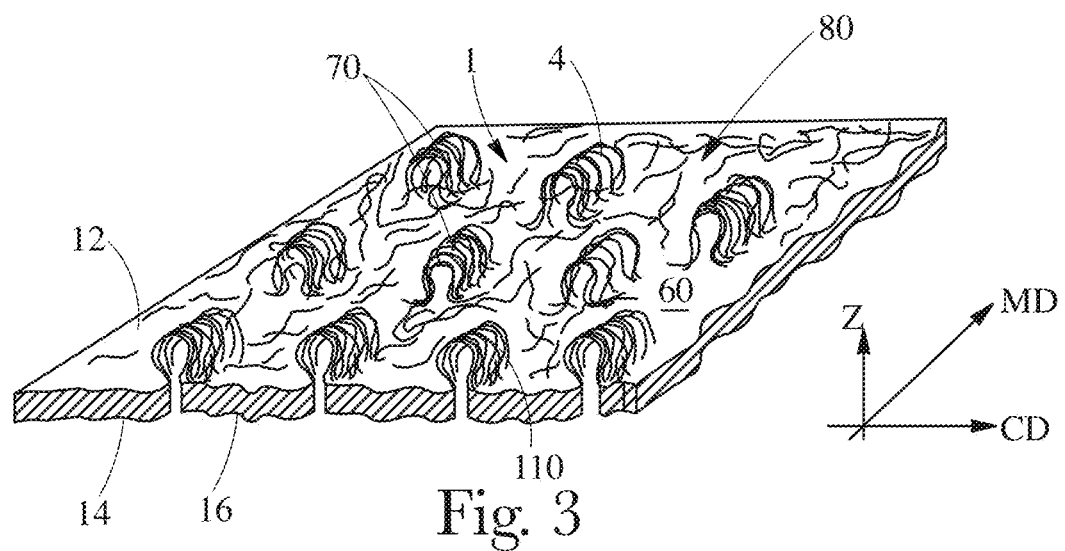
FIG. 3 is a schematic of a fibrous nonwoven web and tufts.

A portion of a topsheet 30 comprising a fibrous nonwoven web 60 and tufts 70 is shown in FIG. 3. The fibrous nonwoven web 60 has a first surface 12 and a second surface 14, a machine direction MD and a cross machine direction CD, and an out of plane Z direction, as is commonly known in the art of nonwoven webs. The first surface 12 can be the body facing surface 120 of the topsheet 30. The fibrous nonwoven web 60 can be comprised of substantially randomly oriented fibers, randomly oriented at least with respect to the MD and CD. By substantially randomly oriented it is meant that, due to processing conditions, there may be a higher amount of fibers oriented in the MD than the CD, or vice-versa. For example, in spunbonding and meltblowing processes, continuous strands of fibers are deposited on a support moving in the MD. Despite attempts to make the orientation of the fibers of the spunbond or meltblown nonwoven web "random," usually a higher percentage of fibers are oriented in the MD as opposed to the CD.

Fibrous nonwoven web 60 can be any known nonwoven web comprising fibers having sufficient elongation properties to be formed into the topsheet 30 described herein. Fibrous nonwoven web 60 can comprise a plurality of tufts 70, the tufts 70 comprising fibers 110 integral with and extending from the fibrous nonwoven web 60. A plurality of the fibers 110 forming the tufts 70 can be looped fibers 110. A discontinuity 16 can be associated with the second surface 14 of the fibrous nonwoven web, the discontinuity 16 resulting from integral extensions of the fibers 110 of the fibrous nonwoven web 60 to form tufts 70.

Tufts 70 can comprise looped fibers 110 that begin and end at the fibrous nonwoven web 60. The looped fibers 110 can be generally aligned with one another within a single tuft 70 in the MD and or CD direction. The tufts 70 can comprise a plurality of looped aligned fibers 110 forming tunnel shaped tufts 70. Tunnel shaped tufts 70 can be open tunnel shaped tufts 70 in which the interior of the tuft 70 is open or generally open, for instance structured such that the tuft 70 has an open interior void space 79 that can be open to or generally open through the tuft 70. Tunnel shaped tufts 70 can be tunnel shaped tufts 70 in which the interior of the tuft comprises fibers 110. Tunnel shaped tufts 70 can act as conduits for fluid transfer from the fluid source to structures deeper within the absorbent article 5, such as absorbent core 20. Tunnel shaped tufts 70 can be desirable on the portion of the topsheet between tuft region lateral boundaries 80 to collect fluid and on the portions of the topsheet laterally beyond the tuft region lateral boundaries 80 to provide a back up structure to capture fluid that might runoff the topsheet 30.

The term fibrous nonwoven web refers to a web having a structure of individual fibers or threads which are interlaid, but not in a repeating pattern as in a woven or knitted fabric, which do not have randomly oriented fibers. Nonwoven webs or fabrics have been formed from many processes, such as, for example, meltblowing processes, spunbonding processes, hydroentangling processes, spunlacing processes, airlaying, and bonded carded web processes. The basis weight of nonwoven fabrics is usually expressed in grams per square meter (gsm) and the fiber diameters are usually expressed in microns. Fiber size can also be expressed in denier. The basis weight of fibrous nonwoven web 60 can range from 10 gsm to 500 gsm. The constituent fibers of fibrous nonwoven web 60 can be comprised of polymers such as polyethylene, polypropylene, polyester, and blends thereof. The fibers 110 can comprise cellulose, rayon, cotton, or other natural materials or blends of polymers and natural materials. The fibers 110 can also comprise a super absorbent material such as polyacrylate or any combination of suitable materials. The fibers 110 can be monocomponent, bicomponent and/or biconstituent, round, non-round fibers (e.g., shaped fibers or capillary channel fibers), and can have major cross-sectional dimensions (e.g., diameter for round fibers) ranging from 0.1-500 microns. For example, one type of fibers 110 suitable for the fibrous nonwoven web 60 includes nanofibers. The constituent fibers of the precursor web may also be a mixture of different fiber types, differing in such features as chemistry, components, diameter, shape, and the like.

The fibrous nonwoven web 60 can comprise fibers having sufficient elongation properties to have portions formed into tufts 70. Tufts are formed by urging fibers 110 out-of-plane in the Z-direction at discrete, localized, portions of the fibrous nonwoven web 60. The urging out-of-plane can be due to fiber displacement, i.e., the fiber is able to move relative to other fibers and be "pulled," so to speak, out-of-plane. For some fibrous nonwoven webs 60, the urging out-of-plane is due to the fibers 110 of tufts 70 having been at least partially plastically stretched and permanently deformed to form tufts 70. The constituent fibers 110 of fibrous nonwoven web 60 can have an elongation to break of at least about 5%, at least about 10%, at least about 25%, at least about 50%, and or at least about 100%. Elongation to break can be determined by tensile testing, such as by use of Instron tensile testing equipment, and can generally be found on material data sheets from suppliers of such fibers or webs. Fibers 110 of fibrous nonwoven web 60 can comprise fibers capable of experiencing sufficient plastic deformation and tensile elongation, or are capable of sufficient fiber mobility, such that looped fibers 110 are formed.

Figure 4:
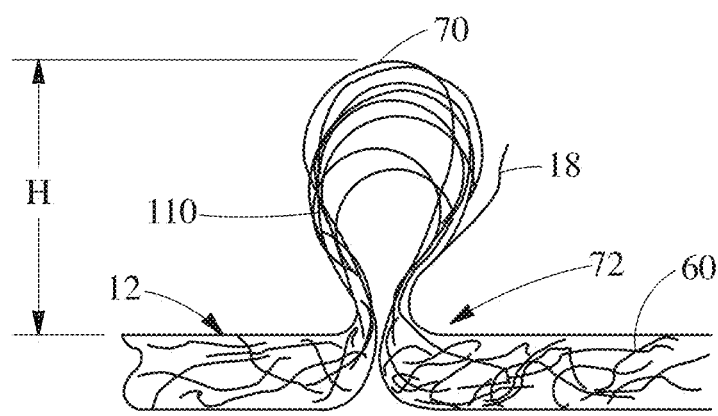
FIG. 4 is a schematic of a cross-section of a tuft.

The term integral refers to fibers 110 of the tufts 70 having originated from the fibrous nonwoven web 60. The looped fibers 110 of the tufts 70 can be plastically deformed and extended fibers 110 of the fibrous nonwoven web 60. Integral is to be distinguished from fibers introduced or added to a separate precursor web for the purpose of making tufts. The average fiber diameter of fibers 110 in the tuft 70 can be less than the average fiber diameter of the fibers 110 in the land area portions 1 of the fibrous nonwoven web 60 from which the tufts 70 extend as a result of the formation process. Some fibers 110 urged out of plane to form tufts 70 may not form loops but may be broken and have loose or broken fiber 18 ends, as shown in FIG. 4.

Tufts 70 can have a tuft height H, measured from the fibrous nonwoven first surface 12 to the apex of the tuft 70. The average height of tufts 70 can be determined based on tufts located in a 1 square centimeter area.

Figure 5:
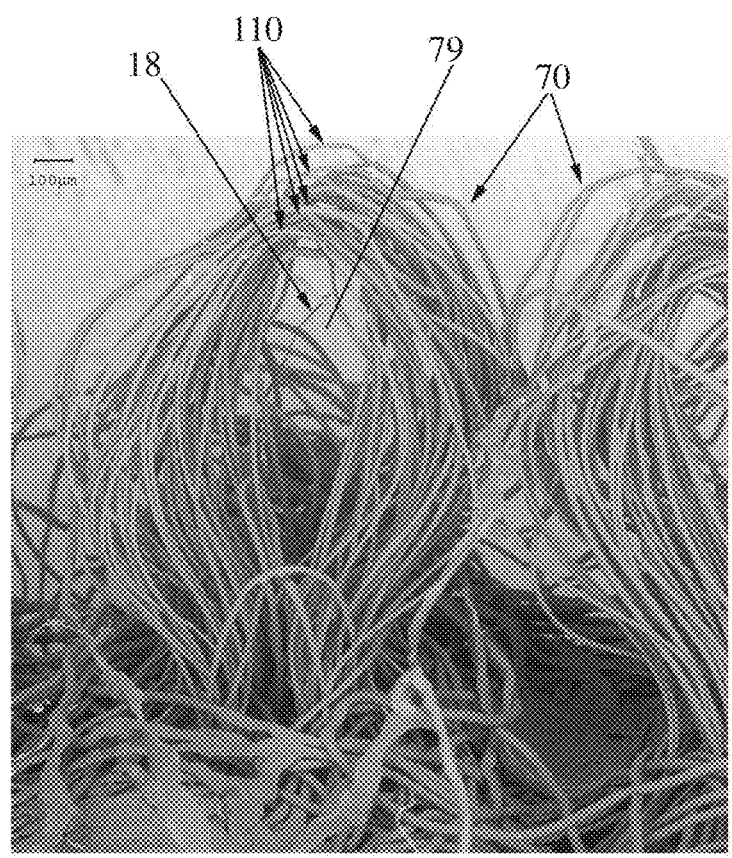
FIG. 5 is a scanning electron micrograph of a tuft.

Tufts 70 can have a tuft base 72. The tuft base is the portion of the tuft 70 proximal the first surface 12 of the fibrous nonwoven web 60. A plurality of looped fibers 110 can converge with one another at the tuft base 72. A scanning electron micrograph of an embodiment of a tuft 70 is shown in FIG. 5. The tufts 70 can function as fluid collectors to transport fluid more deeply into the absorbent core 20, given that the small capillaries at the base of the tufts 70 might generate high suction.

The tuft height H can be greater than about 0.25 mm. The tuft height H can be greater than about 0.5 mm. The tuft height H can be between 0.25 mm and 2 mm. The maximum dimension of a tuft projected onto the MD-CD plane can be at least about 0.4 mm.

The portion of the topsheet 30 comprising tufts 70 can have a tuft area density. The tuft area density is the number of tufts per unit area. The tuft area density can range from 1 tuft per square centimeter to 100 tufts per square centimeter. The tuft area density can be at least 5 tufts per square centimeter. The tuft area density can be determined by counting the number of tufts in a 1 square centimeter area. A greater tuft area density can provide for improved softness, improved stain masking, and/or improved compression resistance.

Tuft region lateral boundaries 80 can be between parts of the topsheet 30 that differ in affinity to water. Affinity to water can be quantified as contact angle of water to the fibers 110 in the fibrous nonwoven web 60. The affinity of fibers 110 for water increases as the contact angle to water of fibers 110 decreases. The affinity to water of fibers 110 can be manipulated by applying a surfactant (hydrophilic or hydrophobic) or lotion (hydrophilic or hydrophobic) to the portions of the fibrous nonwoven web 60 that are desired to have a greater or lesser affinity for water. Affinity to water of fibers 110 can also be manipulated by applying a generally hydrophobic agent to the portions of the fibrous nonwoven web 60 that are desired to have a particular affinity for water. Fibers 110 can be considered to be hydrophilic if the fibers 110 themselves are hydrophilic or rendered to be hydrophilic in some manner. A material can be considered hydrophilic if the material has a static contact angle with water less than 90 degrees or is rendered to have a static contact angle with water less than 90 degrees. Each tuft region lateral boundary 80 can be between a portion of the topsheet 30 comprising a hydrophobic lotion and the longitudinal centerline L. In such an arrangement, lotion can provide for improved wearing comfort of the absorbent article 5. The portion of the fibrous nonwoven web 60 between the tuft region lateral boundaries 80 can be treated with a surfactant to aid in fluid acquisition. Thereby, the tuft region lateral boundaries 80 can serve as a visual cue to the wearer about how much additional fluid capacity the absorbent article might have and the surfactant might help to prevent fluid from spreading from the central part 34 of the topsheet towards parts of the topsheet 30 located more towards the lateral side edges 32 of the absorbent article.

One practical embodiment for topsheet 30 can be one in which the portion of the topsheet 30 between the tuft region lateral boundaries 80 can be relatively hydrophilic as compared to portions of the topsheet 30 outside the tuft region lateral boundaries 80. The portions of the topsheet 30 outside the tuft region lateral boundaries 80 can comprise tufts 70. Such tufts 70 can be relatively hydrophobic (or less hydrophilic) as compared to the portion of the topsheet 30 between the tuft region lateral boundaries 80. This arrangement can provide for a center part 34 of the topsheet 30 that can rapidly acquire fluid and parts of the topsheet 30 beyond the tuft region lateral boundaries 80 can function as a barrier to runoff from the body facing surface 120 of the topsheet 30.

Figure 6:
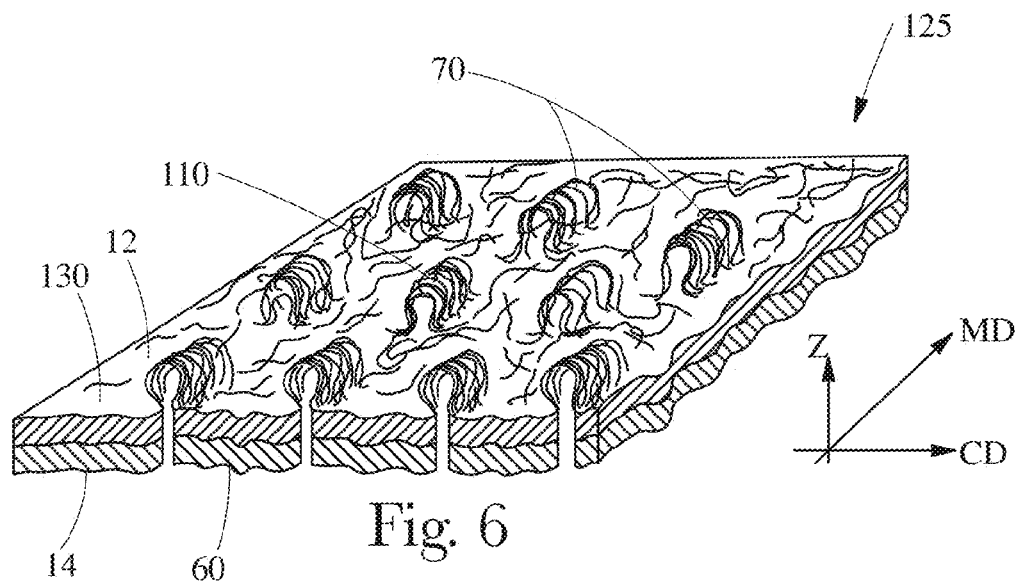
FIG. 6 is a schematic of a laminate having a fibrous nonwoven web and tufts.

The topsheet 30 can comprise a laminate 125 of a fibrous nonwoven web 60 and a polymer film 130, as shown in FIG. 6. The tufts 70 can extend through the polymer film 130. Laminate 125 comprises at least two layers. The layers are generally planar, two-dimensional webs, the length and width of which are substantially greater than the thickness of the individual webs. The fibrous nonwoven web 60 and polymer film 130 can be joined by adhesive, thermal bonding, ultrasonic bonding, and the like or can be joined by the mechanical engagement of the tufts 70 from the fibrous nonwoven web 60 erupting through and or above the first surface 12 of the polymer film 130.

Laminate topsheets can be desirable because such an arrangement allows for the body facing surface 120 of the topsheet 30 to have two different materials presented to the body of the wearer, each of which can provide for a different benefit or function.

Laminate 125 has a first surface 12 and a second surface 14, the first surface 12 and second surface 14 forming sides of the laminate. Each layer of the laminate can have a first surface 12 and second surface 14. Thus, the laminate 125 can be described as being arranged such that the second surface 14 of polymer film 130 is facing the first surface 12 of the fibrous nonwoven web 60. The second surface 12 of fibrous nonwoven web 60 can be facing the absorbent core 20 and can be in fluid communication with the absorbent core 20.

The laminate 125 can have exposed portions of the first surface 12 of the polymer film 130 and a plurality of tufts 70 which are integral extensions of the fibers 110 of the fibrous nonwoven web 60. The tufts 70 can have the same physical structure as the tufts 70 described above for the tufts 70 disposed on the fibrous nonwoven web 60 in which the polymer film 130 is absent.

The polymer film 130 can be any polymer film suitable for employment as a topsheet for an absorbent article 5. The polymer film 130 can have sufficient integrity to be formed into the laminate 125 described herein by the process described herein. The polymer film 130 can have sufficiently lower elongation properties relative to the fibrous nonwoven web 60 such that upon experiencing the strain of fibers 110 from the fibrous nonwoven web 60 being urged out-of-plane in the direction of the polymer film 130, the polymer film 130 will rupture such that fibers 110 from the fibrous nonwoven web 60 can extend through the polymer film 130 to form tufts 70.

Figure 7:
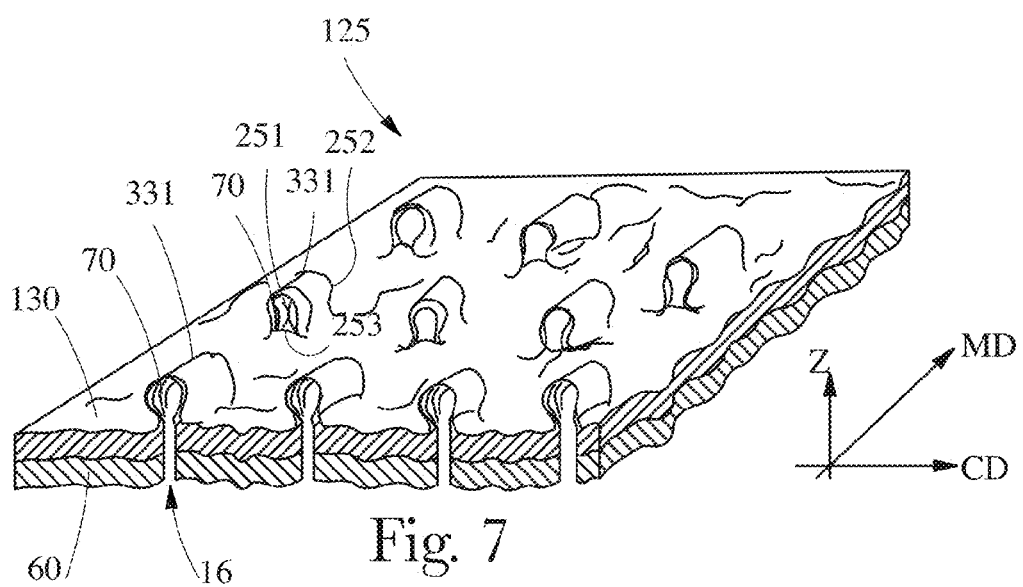
FIG. 7 is a perspective view of a tufted laminate web, the tufts having a cap.
Figure 8:
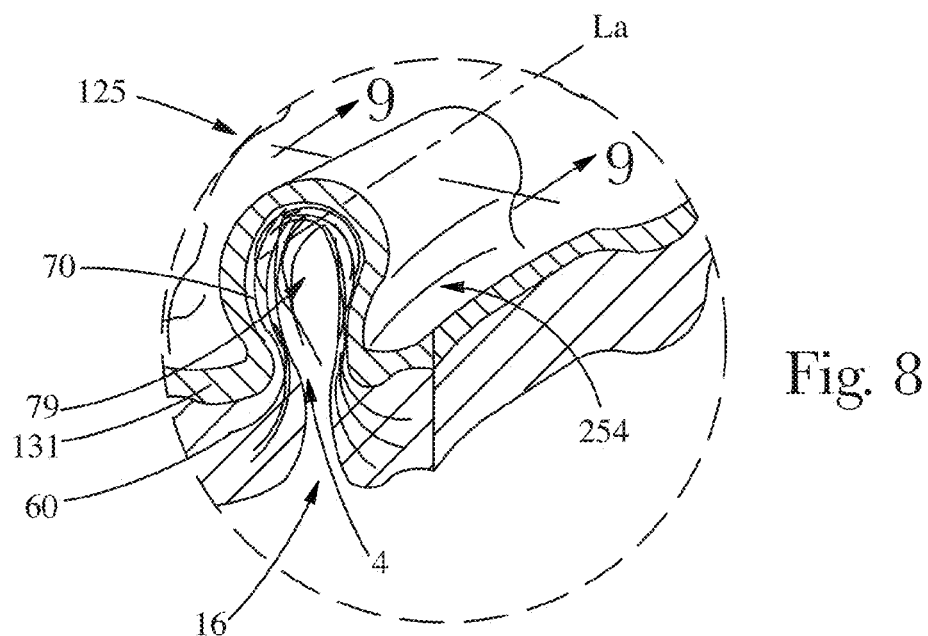
FIG. 8 is an enlarged view of a portion of the web shown in FIG. 7.
Figure 9:
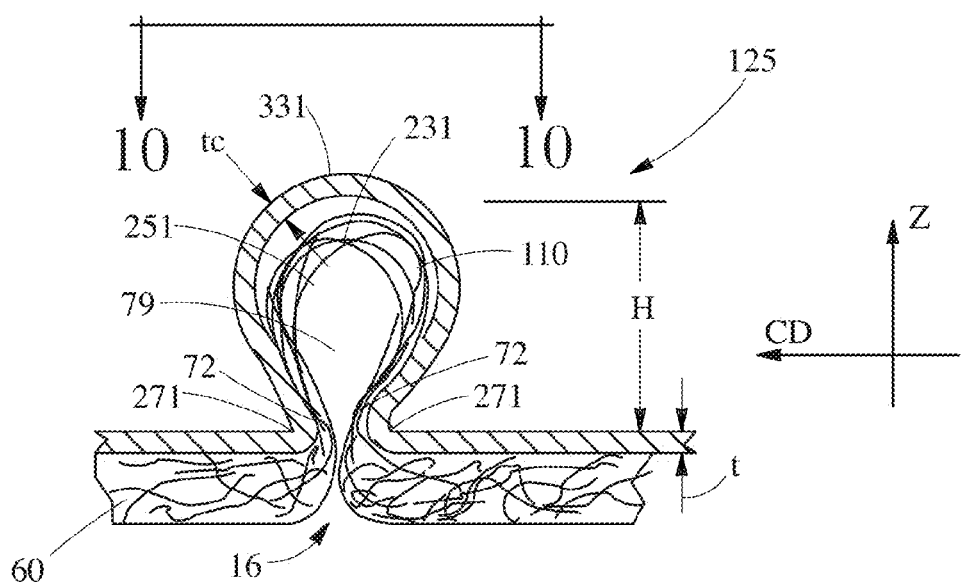
FIG. 9 is a cross-sectional view of section 9-9 of FIG. 8.

The polymer film 130 can rupture such that a cap 331 of polymer film 130 remains over the distal portion of a tuft 70 (e.g. the top of the tuft 70) and a location of rupture 253 is present, the location of rupture providing for a pathway of fluid communication between the first surface 12 of the polymer film and the fibrous nonwoven web 60, as shown in FIG. 7.

The cap 331 can be an integral extension of the polymer film 130. The cap 331 can be a plastically deformed extended substrate of the polymer film 130 and integral with the polymer film 130. Integral, in reference to the cap 331, means originated from the polymer film 130 and is to be distinguished from a substrate introduced to or added to a separate precursor web for the purpose of making a cap.

The polymer film 130 can be microtextured polymer film. By microtextured it is meant that the there are a plurality of microfeatures in the precursor web between the tufts 70, such microfeatures being sized and dimensioned so that a plurality of microfeatures can fit between adjacent tufts 70. That is, the micro features are sized and dimensioned such that the microfeatures can have a maximum dimension smaller than one-half the distance between adjacent tufts 70. The microfeatures can, for example, be microapertures or micro bubbles, examples of which are disclosed in U.S. Pat. No. 7,402,732, issued to Stone et al. and U.S. Pat. No. 4,839,216 issued to Curro et al., U.S. Pat. No. 4,609,518 issued to Curro et al., and U.S. Pat. No. 4,609,518 issued to Curro et al. The polymer film 130 can be an apertured polymer film 130, the apertures of which each have an area of between about 0.01 mm² and about 0.78 mm². The microfeatures can be raised portions. Raised portions can be integral extensions of the polymer film 130 or can be materials added to the surface of the polymer film 130.

Caps 331 are integral extensions of polymer film 130. At least part of a distal portion 231 of each of the tufts 70 can be covered by a cap 331. As shown in FIGS. 7-10, a cap 331 can be a tunnel shaped cap 331 having a first opening 251 and a second opening 252. The first opening 251 comprises a location of rupture 253 in the polymer film 130 and the tuft 70 extends above the location of rupture 253. The caps 331 integrally extend from polymer film 130 proximal the location of rupture 253. The location of rupture 253 may be a point or a line. A cap 331 is formed by rupturing the polymer film 130 at at least one location of rupture 253 and stretching the polymer film 130 out of plane of the first surface 12 of the polymer film 130 to form an opening such as first opening 251 or a first opening 251 and a second opening 252. The location of rupture 253 can define at least part of the boundary of the opening 4. The remainder of the opening 4 can be defined by one or more additional locations of rupture or portions of the cap 331 proximal the location from which the cap 331 integrally extends from the second polymer film 130. The polymer film 130 can be fluid impervious in absence of a location of rupture 253.

The first opening 251 can be arch shaped such that the first opening 251 is broadest proximal the first surface 12 of the polymer film 130 and generally becomes narrower towards the portion of the cap covering the distal portion 231 of the tuft 70. The cap 331 can have a cap base 271 proximal the first surface 12 of the polymer film 130. The cap base 271 can be narrower than a portion of the cap 331 away from the cap base 271. The first opening 251 can be uppercase omega shaped (Ω) such the first opening 251 is narrower proximal the first surface 12 of the polymer film 130 than at a location midway between the tuft base 72 and the distal portion 231 of tuft 70. Similarly, if a second opening 252 is present, second opening 252 can be arch shaped such that the second opening 252 is broadest proximal the first surface 12 of the polymer film 130 and generally narrows towards the portion of the cap 331 covering the distal portion 231 of the tuft 70. The second opening 252 can be uppercase omega shaped (Ω) such that the second opening 252 is narrower proximal the first surface 12 of the polymer film 130 than at a location midway between the tuft base 72 and the distal portion 231 of tuft 70. The second opening 252 can oppose the first opening 251 in that the tuft 70 is between second opening 252 and first opening 251. The first opening 251, the second opening 252, and any additional openings can make the laminate 125 fluid pervious.

If there is a first opening 251 and a second opening 252, the cap 331 can integrally extend from the polymer film 130 at at least two extension locations 254 spaced apart from one another by the first opening 251 and the second opening 252. The at least two extension locations 254 can be at opposing positions on opposing sides of the tuft 70. The cap 331 can integrally extend from the polymer film 130 at at least two extension locations 254, each extension location 254 adjacent a location of rupture 253. In addition to a first opening 251 and a second opening 252, there can be additional openings. For instance, if there are three or more openings (e.g., first opening 251, second opening 252, and third opening), the cap 331 can integrally extend from the polymer film 130 at at least three extension locations 254 spaced apart from one another by the openings (e.g. first opening 251, second opening 252, and third opening).

Figure 10:
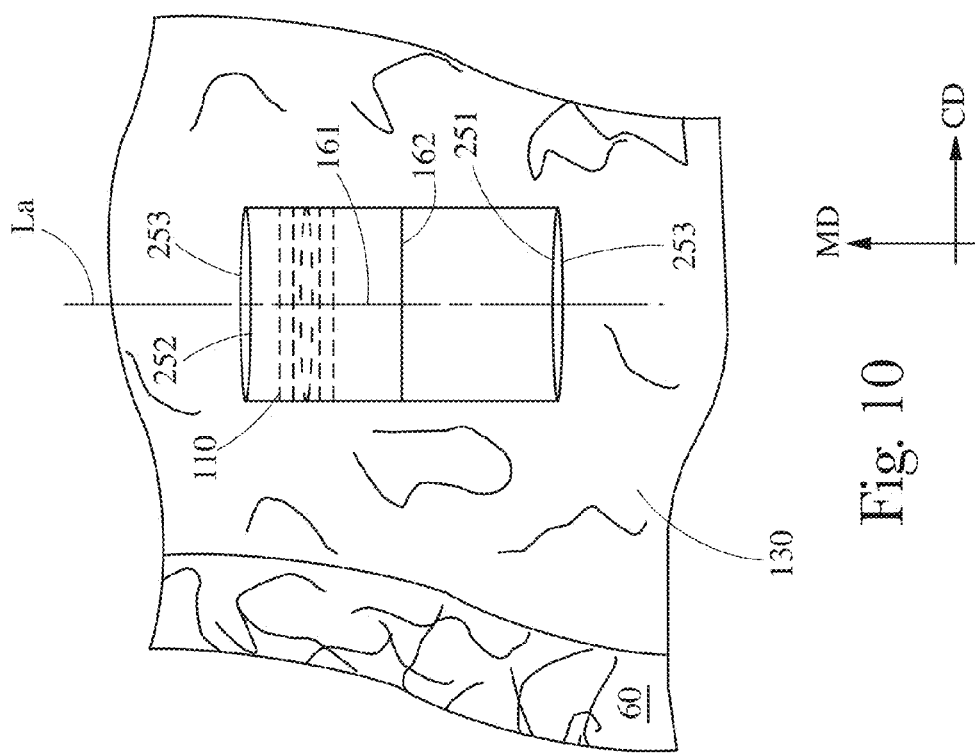
FIG. 10 is a plan view of a portion of the web shown in FIG. 9.

As shown in FIG. 10, cap 331 can have cap length 161 and a cap width 162. The cap length 161 of cap 331 is taken to be between the first opening 251 and second opening end 252. Cap 331 can also have a cap width 162 taken to be the maximum dimension of the cap 331 as measured orthogonal to the cap length 161 of the cap 331. The plane aspect ratio of the cap 331 can be defined as the ratio between the cap length 161 and the cap width 162 of cap 331. The aspect ratio of the cap 331 can be greater than about 0.5. The aspect ratio of the cap 331 can be greater than about 1. The aspect ratio of the cap 331 can be greater than about 1.5. The aspect ratio of the cap 331 can be greater than about 2. In general, it is thought that caps 331 having a higher aspect ratio can be more noticeable to an observer of the laminate 125 and might also better resist fluid flow along the surface of web 1 in a direction orthogonal to the long axis La of the tuft 70.

Caps 331 in laminate 125 are thought to mask or partially mask fluid that is collected by the laminate 125 and remains in the capillaries between fibers 110 forming tuft 70. Such a laminate web employed in an absorbent article such as a wipe, a sanitary napkin, a tampon, or a diaper can be appealing to the user (or caregiver) in that potentially unsightly urine, menses, feces, or other liquid retained in the capillaries between fibers 110 forming tuft 70 will be obscured or partially obscured from the viewer. In an absorbent article such as a sanitary napkin, in absence of the caps 331, tufts 70 can essentially have the color of menses, which might be unattractive to the user of the sanitary napkin. The caps 331 cover or partially cover tufts in which menses is held and can make the laminate 125 appear less red or even allow the laminate 125 to maintain its virgin color (e.g. prior to insult by a fluid).

If the polymer film 130 and cap 331 extending there from is a polymer film comprising a whitener, such as titanium dioxide, the caps 331 can be more effective at obscuring materials held in the capillaries of the tufts 70 from view. Such caps 331 can better maintain a perceived color of white, which many consumers associate with cleanliness.

The caps 331 can have an opacity greater than about 10%, greater than about 20%, greater than about 30%, greater than about 40%, greater than about 50%, greater than about 60%, greater than about 70%, greater than about 80%, or greater than about 90%. The caps 331 can be opaque. The polymer film 130 can have an opacity. The opacity of the caps 331 can be less than the opacity of the polymer film 130 from which the caps 331 extend, for instance as a result of stretching of the polymer film to form cap 331. The caps 331 can have an opacity that is between about 80% and about 95% of the opacity of the second precursor web. The caps 331 can have an opacity that is between about 50% and about 95% of the opacity of the polymer film 130. The caps can have an opacity that is between about 35% and about 95% of the opacity of the polymer film 130. The greater the opacity of the caps 331, the more effective the caps 331 might be at obscuring liquids that held in the capillaries of the tufts 70. The caps 331 can have an opacity less than about 90% of the opacity of the polymer film 130. The caps 331 can have an opacity less than about 75% of the opacity of the polymer film 130. The caps 331 can have an opacity less than about 50% of the opacity of the polymer film 130.

As used herein, the term "opacity" refers to the property of a substrate or printed substrate which measures the capacity of the substrate to hide or obscure from view an object placed behind the substrate relative to point from which observation is made. Opacity can be reported as the ratio, in percent, of the diffuse reflectance of a substrate backed by a black body having a reflectance of 0.5% to the diffuse reflectance of the same substrate backed with a white body having an absolute reflectance of 89%. Opacity can be measured as described in ASTM D 589-97, Standard Test Method for Opacity of Paper (15°/Diffuse Illuminant A, 89% Reflectance Backing and Paper Backing).

A substrate high in opacity will not permit much, if any, light to pass through the substrate. A substrate having low opacity will permit much, if not nearly all, light to pass through the substrate. Opacity can range from 0 to 100%. As used herein, the term "low opacity" refers to a substrate or printed substrate having opacity less than 50%. As used herein, the term "high opacity" refers to a substrate or printed substrate having opacity greater than or equal to 50%. As used herein, the term "opaque" refers to a substrate or printed substrate that has an opacity greater than or equal to 50%.

Polymer film 130 can have a polymer film thickness t and the cap 331 can have a cap thickness tc. Being that the caps 331 are integral extensions of the polymer film 130 and formed by stretching the polymer film 130 out of plane of the first surface 12 of the polymer film 130, the cap thickness tc of a portion of the cap 331 can be less than the polymer film thickness t. That is, the polymer film that is extended to form a cap 331 is thinned at at least some portion of the cap 331 relative to the planar portion of the polymer film from which the cap 331 extends. The cap thickness tc may not be uniform about the entire first opening 251 and/or second opening 252. The cap thickness tc at a distal portion of the cap 331 may be the same or less than the polymer film thickness t. The cap thickness tc at a distal portion of the cap 331 may be about the same or less than the polymer film thickness t and the cap thickness tc at a portion of the cap 331 between the distal portion of the cap 331 and the polymer film 130 may be less than the polymer film thickness t. Thinning of the cap 331 may provide for caps 331 having a soft hand. Further, because the cap 331 might be thin and might readily be deformed, the characteristics of the tuft 70 underlying the cap 331 might govern the tactile impression imparted by the tuft 70 having a cap 331. Therefore, the characteristics of the tuft 70 can be important to the tactile impression imparted by the laminate 125.

Tufts 70 erupting from fibrous nonwoven web 60 can be mechanically engaged with the polymer film 130 as the cap base 271 can constrict upon the tuft 70 (and/or second tuft). This indicates a certain amount of recovery at the cap base 271 that can tend to constrain tuft 70 from pulling back through the polymer film 130. There can be a plurality of tufts 70 that are closely spaced to one another such that the tufts 70 substantially cover the polymer film 130. Such an arrangement can provide a composite topsheet 30 that presents a film as the body-facing surface 120 in some parts of the topsheet 30 and presents a nonwoven as the body facing surface 120 in other parts of topsheet 30.

The fibrous nonwoven web 60 can be relatively hydrophilic as compared to the polymer film 130. That is, the fibrous nonwoven web can have a contact angle to water less than the contact angle to water of the polymer film 130. The contrast in the fluid interaction properties of the substrates can be controlled as part of the process of selecting the materials and/or applying chemical treatments to the materials themselves. A relatively hydrophilic fibrous nonwoven web 60 can act to draw fluid into the absorbent article 5. A relatively hydrophobic polymer film 130 can feel dry to the wearer of the absorbent article.

Figure 11:
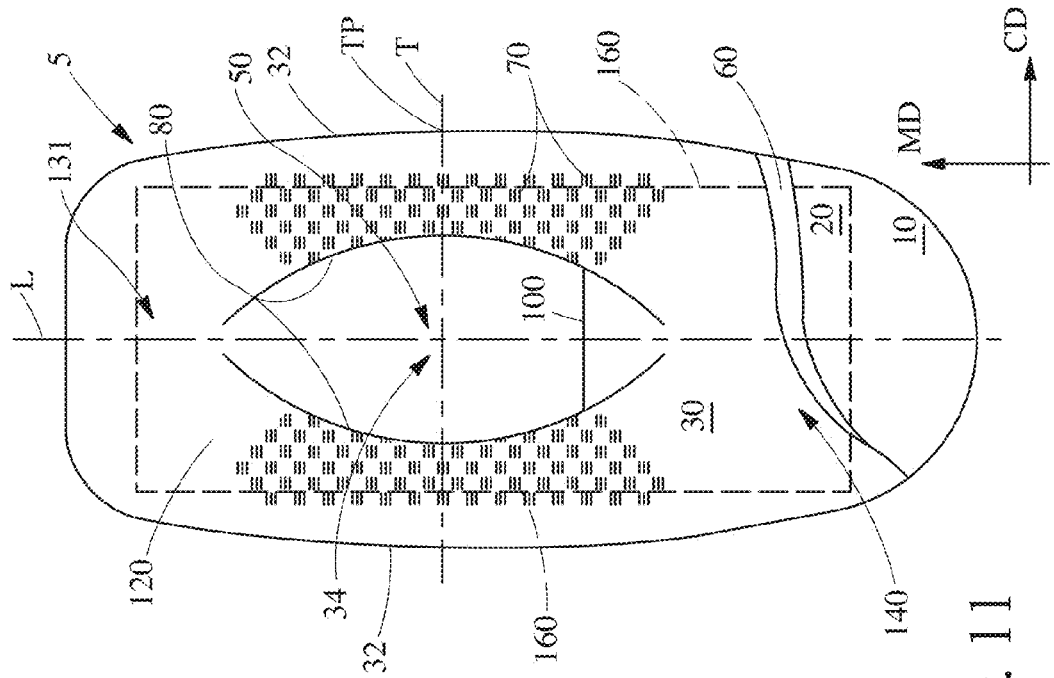
FIG. 11 is a schematic top cutaway view of an absorbent article, the topsheet formed by a laminate.

A cutaway view of an absorbent article 5 comprising a topsheet 30 having a laminate 125 of a fibrous nonwoven web 60 and a polymer film 130 is shown in FIG. 11. Polymer film can be an apertured film such as that known as DRI-WEAVE®, employed in ALWAYS® Ultra Thin sanitary napkins and polymer films described in U.S. Pat. No. 4,342,314 issued to Radel et al., U.S. Pat. No. 4,463,045 issued to Ahr et al., U.S. Pat. No. 7,402,723, issued to Stone et al., and U.S. Pat. No. 4,629,643, issued to Curro et al.

An embodiment in which the tuft region lateral boundaries 80 are spaced apart from each other by a distance 100 that is gradually decreasing from a maximum at the parallel transverse axis TP to a minimum at one or both of the longitudinally opposing ends of the tuft region lateral boundaries 80, as shown in FIG. 11, can also be practical. The distance 100 can gradually decrease as a function of location along the longitudinal centerline L such that portions of the tuft region lateral boundaries 80 are straight or curved. The ends of the tuft region lateral boundaries 80 need not necessarily be free ends beyond which the topsheet 30 is devoid of tufts. For instance, the part of the topsheet 30 between the tuft region lateral boundaries 80 can comprise tufts 70 and the part of the topsheet 30 between the tuft region lateral boundaries 80 can be surrounded by a part of the topsheet 30 devoid of tufts 70. That is, the portion of the topsheet 30 between the tuft region lateral boundaries can be an island comprising a plurality of tufts 70 surrounded by a portion of the topsheet 30 devoid of tufts 70. Such an arrangement might provide comfort to the wearer's labial region from soft and supple tufts 70.

Tuft region lateral boundaries 80 that are spaced apart from each other by a distance 100 that is gradually decreasing from a maximum at the parallel transverse axis TP to a minimum at one or both of the longitudinally opposing ends of the tuft region lateral boundaries 80 are thought to possibly provide a number of benefits. For instance, the labial region of a woman's crotch can be generally shaped such that it is somewhat narrow towards the woman's front and back and broader between the front part of the labia and the rear part of the labia. Thus, the portion of the topsheet 30 between the tuft region lateral boundaries 80 can be arranged to have the same plan shape as the woman's labial region. Such area can be provided with tufts 70 that are soft and might help capture fluid. Alternatively, tufts 70 might be provided between the tuft region lateral boundaries 80 and the lateral side edges 32 of the absorbent article to resist lateral flow of fluid off the surface of the topsheet 30. Furthermore, stain patterns on absorbent articles 5 resulting from discharge from the wearer's body can be somewhat oval shaped with the long axis of the oval generally aligned with the wearer's crotch from her front to her back. Thus, the portion of the topsheet 30 between the tuft region lateral boundaries 80 can be arranged to have a shape that is broadest at the parallel transverse axis TP and is tapered towards the longitudinally opposing ends of the region between the tuft region lateral boundaries 80. The location of the stain relative to the tuft region lateral boundaries 80 can provide the wearer with a visual cue as to whether she needs to change her absorbent article 5.

The topsheet 30 can comprise a laminate 125 of a fibrous nonwoven web 60 and a second nonwoven web, the second nonwoven web being substituted for the polymer film 130 illustrated in FIG. 6. The tufts 70 can extend through the second nonwoven web. Laminate 125 comprises at least two layers. The layers are generally planar, two-dimensional webs, the length and width of which are substantially greater than the thickness of the individual webs. The fibrous nonwoven web 60 and second nonwoven web can be joined by adhesive, thermal bonding, ultrasonic bonding, and the like or can be joined by the mechanical engagement of the tufts 70 from the fibrous nonwoven web 60 erupting through the second nonwoven web. The fibrous nonwoven web 60 can be relatively hydrophilic as compared to the second nonwoven to aid in drawing fluid more deeply into the absorbent article 5.

Figure 12:
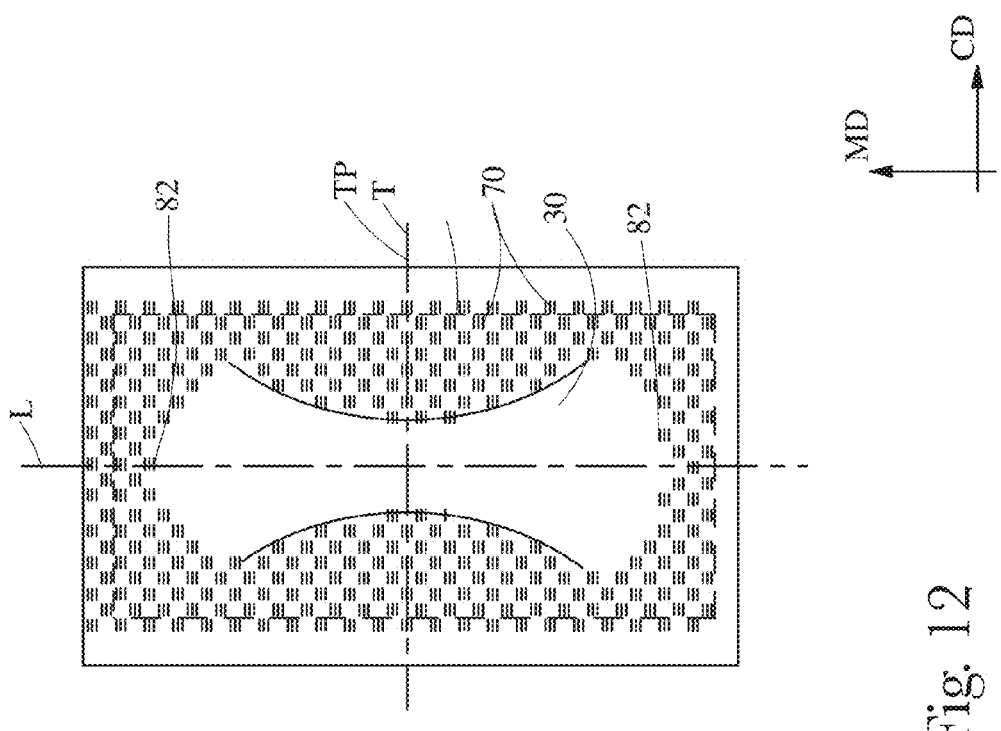
FIG. 12 is a schematic top view of an absorbent article.

The longitudinally opposing ends 81 of the tuft region lateral boundaries 80 need not necessarily be free ends beyond which the topsheet 30 is devoid of tufts 70. As shown in FIG. 12, a part of the topsheet 30 between the tuft region lateral boundaries 80 can be devoid of tufts 70 and the part of the topsheet 30 between the tuft region lateral boundaries 80 can be surrounded by a part of the topsheet 30 comprising the tufts 70. That is, the portion of the topsheet 30 between the tuft region lateral boundaries 80 can be an island devoid of tufts 70 surrounded by a sea of tufts 70. In such an arrangement, the out of plane structure of the tufts 70 can be employed to reduce the potential for fluid to run off the topsheet 30 and to provide comfort to the wearer in areas of the topsheet 30 away from the most central portion of the topsheet 30 that come in contact with the wearer's labia.

A tuft region end boundary 82 can connect tuft region lateral boundaries 80 that are on opposing sides of the longitudinal centerline L. The tuft region end boundary 82 can be defined by a line or portion of a line separating a plurality of the tufts 70 from a portion of the topsheet that is devoid of tufts 70.

A tuft region lateral boundary 80 can be only that portion of the boundary between a portion of the topsheet 30 comprising a plurality of tufts 70 and a portion of the topsheet 30 devoid of the tufts 70 such that the distance between tuft region lateral boundaries 80 gradually increases from a minimum at the parallel transverse axis TP to a maximum at one or both of the longitudinally opposing ends of the tuft region lateral boundaries 80. Thus, in FIG. 12, the tuft region end boundaries 82 can be considered to not be part of the tuft region lateral boundaries 80 because if the parts of the tuft region end boundaries 82 were considered as such, the distance between the tuft region lateral boundaries 80 would not be spaced apart from each other by a distance gradually increasing from a minimum at the parallel transverse axis TP to a maximum at one or both longitudinally opposing ends of the tuft region lateral boundaries 80.

Figure 13:
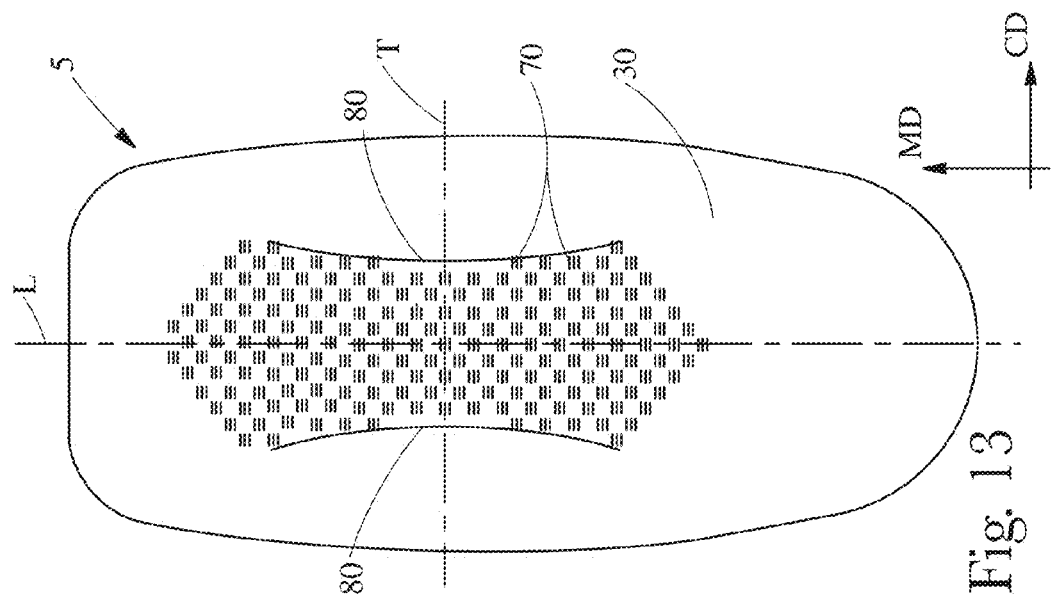
FIG. 13 is a schematic top view of an absorbent article.

The longitudinally opposing ends 81 of the tuft region lateral boundaries 80 need not necessarily be free ends beyond which the topsheet 30 comprises a plurality of tufts 70. For instance, as shown in FIG. 13, a part of the topsheet 30 between the tuft region lateral boundaries 80 can comprise tufts 70 and the part of the topsheet 30 between the tuft region lateral boundaries 80 can be surrounded by a part of the topsheet 30 devoid of tufts 70. That is, the portion of the topsheet 30 between the tuft region lateral boundaries 80 can be an island comprising a plurality of tufts 70 surrounded by a portion of the topsheet 30 devoid of tufts 70. In such an arrangement, the out of plane structure of the tufts 70 can be employed to provide for a comfortable surface texture on the portion of the topsheet 30 that might come into contact with the wearer's labia.

Topsheets 30 of absorbent articles 5 are often white to connote the cleanliness of the absorbent article 5 prior to use or in use. If the fibrous nonwoven web 60 used as the topsheet 30 is white, tufts 70 on the nonwoven web can be difficult for the user to visually discern. Providing color to the portion of the topsheet 30 comprising tufts 70 might make it easier for the wearer to discern that portion against the portion of the topsheet 30 devoid of the tufts 70. For embodiments comprising a portion of the topsheet 30 devoid of the tufts 70 that is an island surrounded by a sea of tufts 70, providing a difference in color between the portion of the topsheet 30 comprising tufts 70 and the portion of the topsheet 30 devoid of tufts 70 can provide the wearer with visual cues and boundaries to more easily assess whether the used absorbent article 5 needs to be exchanged for a fresh absorbent article 5. Color can be provided to the tufts by printing on the tufts 70 by laser printing, inkjet printing, rotogravure printing, or other suitable printing technology.

In some embodiments, a plurality of the tufts 70 have a first color 157 and the portion of the topsheet 30 devoid of the tufts 70 has a second color 151, as shown in FIG. 14. The first color 157 can differ from the second color 151. The difference in color can be greater than about 3.5, as characterized by the CIE LAB scale. The difference in color can be greater than about 1.1, as characterized by the CIE LAB scale. The difference in color can be greater than about 6, as characterized by the CIE LAB scale. The difference in color can be at least 1.1, as characterized by the CIE LAB scale.

A difference in color can be characterized using the CIE LAB scale and measured using a Hunter Labscan XE 45/0 geometry reflectance spectrophotometer. Technical description of the system can be found in an article by R. S. Hunter, 'photoelectric color difference Meter', Journal of the Optical Society of America, Vol. 48, pp. 985-95, 1958. Devices that are specially designed for the measurement of color on the Hunter scales are described in U.S. Pat. No. 3,003,388 to Hunter et al., issued Oct. 10, 1961.

Colors can be measured according to an internationally recognized 3D solid diagram of colors where all colors that are perceived by the human eye are converted into a numerical code. The CIE LAB system is similar to Hunter L, a, and b and is based on three dimensions, specifically L*, a*, and b*.

When a color is defined according to this system L* represents lightness (0=black, 100=white), a* and b* independently each represent a two color axis, a* representing the axis red/green (+a=red, −a=green), while b* represents the axis yellow/blue (+b=yellow, −b=blue).

A color may be identified by a unique ΔE value (i.e., different in color from some standard or reference), which is mathematically expressed by the equation:

$$\Delta E^* = [(L^*X - L^*Y)^2 + (a^*X - a^*Y)^2 + (b^*X - b^*Y)^2]^{1/2}$$

'X' represents the standard or reference sample and 'Y' is the variant.

The Hunter color meter is configured to yield 3 values (L*, a*, b* and ΔE* which is total color). The L* value is the percent of the incident (source) light that is reflected off a target sample and onto the detector. A shiny white sample will yield an L* value near 100. A dull black sample will yield an L* value of about 0. The a* and b* value contains spectral information for the sample. Positive a* value indicates the amount of green in the sample.

The diameter of the port is to be selected based on the area upon which color measurement is to be made, with the size of the port being the largest port available that provides for an area view that is smaller than the area upon which color measurement is made. A 0.2 inch diameter port can be used. A 0.7 inch diameter port can be used having a 0.5 inch area view. The instrument is to be calibrated using standard white and black tiles supplied by the instrument manufacturer prior to use for measurements.

A standard, industry-recognized procedure is used to measure the L*, a*, and b* values. The color of parts of the topsheet is measured using a reflectance spectrophotometer in accordance with method ASTM E 1164-94, "Standard Practice for Obtaining Spectrophotometric Data for Object-Color Evaluation". This standard method is followed but specific instrument settings and sampling procedure are given here for clarity. Sample color can be reported in terms of the CIE 1976 color coordinate standard as specified in ASTM E 1164-94 and ASTM D2264-93, section 6.2. This consists of three values; L* which measures sample "lightness", a* which measures redness or greenness, and b* which measures yellowness or blueness.

Apparatus

Reflectance Spectrophotometer . . . 45°/0° Hunter Labscan XE, or equivalent

HunterLab Headquarters, 11491 Sunset Hills Road, Reston Va. 20190-5280 Tel: 703-471-6870 Fax: 703-471-4237, http://www.hunterlab.com.

Standard plate . . . Standard Hunter White Tile Source: Hunter Color.

Equipment Preparation

1. Assure that the Spectrophotometer is configured as follows:
  Illumination . . . Type C
  Standard Observer . . . 2°
  Geometry . . . 45/0° Measurement angle
  Port Diameter . . . select port diameter based upon the area upon which color measurement is to be made
  Viewing area . . . to be selected based upon the area upon which color measurement is to be made
  UV Filter: Nominal 2. Calibrate the spectrophotometer using standard black and white tiles supplied with the instrument according to manufacturer's instructions before beginning any testing.

Sample Preparation

1. Unwrap, unfolded and lay the product or article samples flat without touching or altering the color of the body facing surface.

2. Areas on the viewing surface of the product should be selected for measurement and must include the following:
  The reference region of the viewing surface.
  The variant region of the viewing surface.
  Any other portions of the viewing surface having a visibly or measurably different color from the reference or variant region. Measurements should not be made overlapping the border of two shaded portions.

Test Procedure

1. Operate the Hunter Colorimeter according to the instrument manufacturer's instructions.

2. The absorbent article should be measured laying flat over the aperture on the instrument. A white tile should be placed behind the pad.

3. The absorbent article should be placed with its long direction perpendicular to the instrument.

4. Measure the same zones selected above for at least 3 replicate samples.

Calculation Reporting

1. Ensure that the reported results are really CIE L*, a*, b*.

2. Record the L*, a*, b* values to the nearest 0.1 units.

3. Take the average L*, a*, b* for each zone measured.

4. Calculate ΔE* between a colored region and the background.

As shown in FIG. 15, the absorbent core can have a pair of core lateral edges 160 spaced away from the longitudinal centerline L. The tuft region lateral boundaries 80 and absorbent core 20 can be sized and dimensioned such that neither of the tuft region lateral boundaries 80 extend beyond the core lateral edges 160 of the absorbent core 20. Such an arrangement can provide the wearer with a visual cue that it is time to change her absorbent article 5. For instance, if the wearer checks her absorbent article 5 and sees that stain area caused by discharge from her body is approaching one or both of the tuft region lateral boundaries 80 or is outside the confines of the tuft region lateral boundaries 80 (i.e. fluid may be encroaching towards one or both of the core lateral edges 160), she can discern that the absorbent core 20 might be approaching its designed fluid capacity and it is time to change her absorbent article 5. By having the tuft region lateral boundaries 80 inboard of the core lateral edges 160, the wearer will be provided with a benefit in case she is late to recognize that the fluid is approaching or past the tuft region lateral boundaries 80. That is, the absorbent core might still have some additional storage capacity in the event that the stain has advanced laterally beyond one or both tuft region lateral boundaries 80. The tuft region lateral boundaries 80 might be discernable based upon the difference in the visual appearance of the stain in the non-tufted portion of the topsheet 30 and the portion comprising tufts 70 or the difference in appearance in the absence of a stain due to a different surface texture presented to the wearer.

Tufts 70 in fibrous nonwoven web 60 can be formed using any of a variety of methods. Methods of producing the tufts 70 include, but are not limited to needle punching, creping, hydroentangling, intermeshing rolls having teeth disposed thereon, and combinations thereof.

A variety of nonwoven webs 60 having tufts 70 and methods of making such webs, including laminate webs are disclosed in U.S. Pat. No. 7,410,683 issued to Curro et al., U.S. Patent Pub. No. 2004/0131820 by Turner et al., U.S. Patent Pub. No. 2007/0116926 by Hoying et al., U.S. Patent Pub. No. 2006/0019056 by Turner et al., U.S. Patent Pub. No. 2005/0281976 by Curro et al., and U.S. Patent Pub. No. 2006/0286343 by Curro et al.

Figure 16:
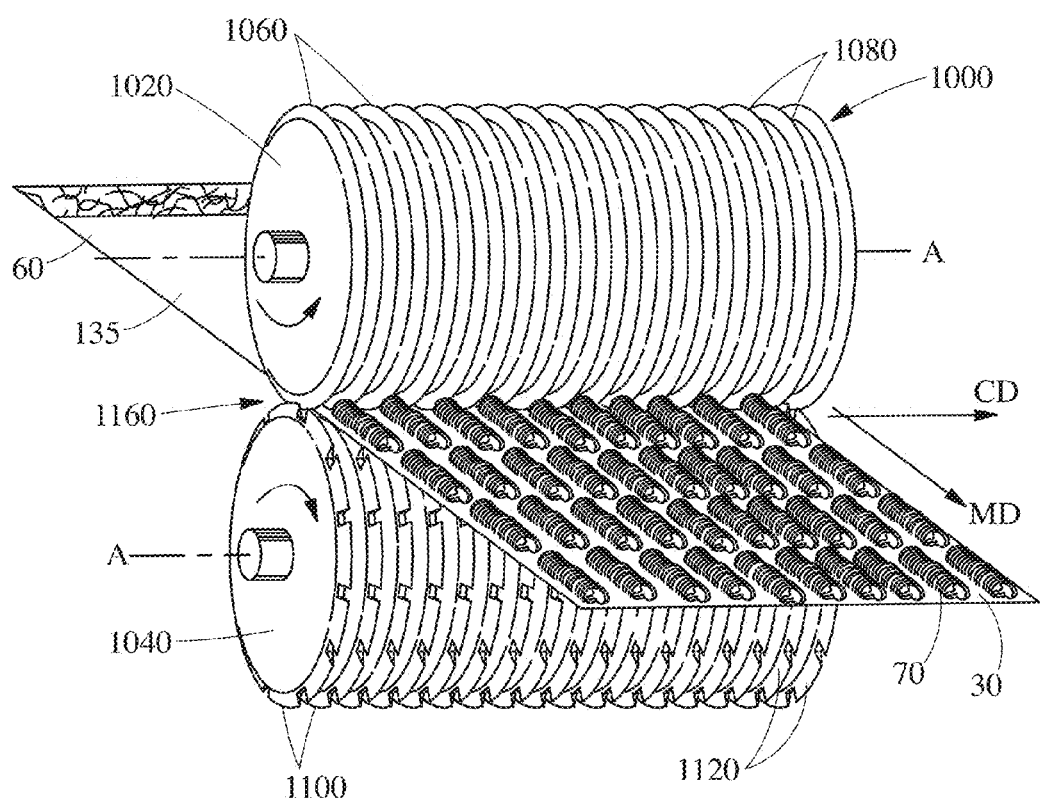
FIG. 16 is a schematic of an apparatus for forming tufts.

Referring to FIG. 16 there is shown in an apparatus and method for making a topsheet 30 comprising a fibrous nonwoven web 60 and tufts 70. The apparatus 1000 comprises a pair of intermeshing rolls 1020 and 1040, each rotating about an axis A, the axes A being parallel in the same plane. Roll 1020 comprises a plurality of ridges 1060 and corresponding grooves 1080 which extend unbroken about the entire circumference of roll 1020. Roll 1040 is similar to roll 1020, but rather than having ridges that extend unbroken about the entire circumference, roll 1040 comprises a plurality of rows of circumferentially-extending ridges that have been modified to be rows of circumferentially-spaced teeth 1100 which extend in spaced relationship about at least a portion of roll 1040. The individual rows of teeth 1100 of roll 1040 are separated by corresponding grooves 1120. In operation, rolls 1020 and 1040 intermesh such that the ridges 1060 of roll 1020 extend into the grooves 1120 of roll 1040 and the teeth 1100 of roll 1040 extend into the grooves 1080 of roll 1020 and form nip 1160. Both or either of rolls 1020 and 1040 can be heated by means known in the art such as by using hot oil filled rollers or electrically-heated rollers. The teeth 1100 can be arranged on roll 1040 to correspond with the desired shape of the tuft region lateral boundaries 80 and location of tufts 70 relative to the tuft region lateral boundaries 80. That is, portions on roll 1040 devoid of teeth can correspond with portions of the topsheet devoid of tufts and portions on roll 1040 having teeth can correspond with portions of the topsheet having tufts 70.

Topsheet 30 can be made by mechanically deforming fibrous nonwoven web 60 or a laminate of fibrous nonwoven web 60 and a second web 135. Second web 135 can be polymer film 130 or second nonwoven web. The teeth 1100 of roll 1040 have a specific geometry associated with the leading and trailing edges that permit the teeth to essentially "punch" through fibrous nonwoven web 60 or a laminate of fibrous nonwoven web 60 and second web 135. In a two layer laminate 125, the teeth 1100 urge fibers from fibrous nonwoven web 60 simultaneously out-of-plane and through second web 135. Second web 135 is punctured, so to speak, by the teeth 1100 pushing the fibers 110 through to form tufts 70.

Fibrous nonwoven web 60 and any other layers present in the topsheet 30 can be provided from supply rolls and moved in a direction towards the nip 1160 of counter-rotating intermeshing rolls 1020 and 1040. The fibrous nonwoven web 60 and other layers present can be held in sufficient web tension so as to enter the nip 1160 in a generally flattened condition by means known in the art of web handling. As fibrous nonwoven web 60 passes through the nip 1160, the teeth 1100 of roll 1040, which are intermeshed with grooves 1080 of roll 1020, urge portions of the fibrous nonwoven web 60 out of the plane of the web to form tufts 70. If a laminate 125 topsheet 30 is desired, as the laminate 125 passes through the nip 1160, the teeth 1110 of roll 1040, which are intermeshed with grooves 1080 of roll 1020, urge portions of the fibrous nonwoven web 60 out of the plane of the web and through second web 135 to form tufts 70. In effect, teeth 1100 "push" or "punch" fibers of fibrous nonwoven web 60 through the second web 135.

As the tip of teeth 1100 push through fibrous nonwoven web 60, the portions of the fibers of fibrous nonwoven web 60 that are oriented predominantly in the CD across teeth 1100 are urged by the teeth 1100 out of the plane of fibrous nonwoven web 60. Fibers can be urged out of plane due to fiber mobility, or they can be urged out of plane by being stretched and/or plastically deformed in the Z-direction. For a laminate 125 topsheet 30, tufts 70 can be formed thereby on the first surface 12 of the laminate 125.

It can be appreciated by the forgoing description that when topsheet 30 is a laminate 125, the fibrous nonwoven web 60 and second web 135 should possess differing material properties with respect to the ability of the materials to elongate before failure, e.g., failure due to tensile stresses. In particular, the fibrous nonwoven web 60 can have greater fiber mobility and/or greater fiber elongation characteristics relative to second web 135 such that the fibers thereof can move or stretch sufficiently to form tufts 70 while the additional layer ruptures, i.e., does not stretch to the extent necessary to form tufts 70.

The degree to which the fibers of fibrous nonwoven webs 60 are able to extend out of plane without plastic deformation can depend upon the degree of inter-fiber bonding of the precursor web. For example, if the fibers of a fibrous nonwoven web 60 are only very loosely entangled to each other, they will be more able to slip by each other and therefore be more easily extended out of plane to form tufts 70. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, fibrous nonwoven web 60 can be a fibrous nonwoven web having relatively low inter-fiber bonding and second nonwoven web, if present, can be a nonwoven web having relatively high inter-fiber bonding, such that the fibers of fibrous nonwoven web 60 can extend out of plane, while the fibers of second nonwoven web cannot.

For a topsheet 30 formed of a laminate 125, the second web 135 can actually fail under the tensile loading produced by the imposed strain. That is, for the tufts 70 to be disposed on the first side 12 of laminate 125, the second nonwoven web or polymer film 130, whichever is present, can have sufficiently low fiber mobility (if any) and/or relatively low elongation-to-break such that it locally (i.e., in the area of strain) fails in tension, thereby producing openings through which tufts 70 can extend. In one embodiment, the second web 135 has an elongation to break in the range of 1%-5%. While the actual required elongation to break depends on the strain to be induced to form the topsheet 30, it is recognized that for some embodiments second web 135 can exhibit a web elongation-to-break of about 6%, about 7%, about 8%, about 9%, about 10%, or more. It is also recognized that actual elongation-to-break can depend on the strain rate, which, for the apparatus shown in FIG. 16 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

For a topsheet 30 that is a laminate 125 of fibrous nonwoven web 60 and second web 135, second web 135 should have lower fiber mobility (if any) and/or lower elongation-to-break (i.e., elongation-to-break of individual fibers, or, if a film, elongation-to-break of the film) than fibrous nonwoven web 60 so that, rather than extending out-of-plane to the extent of the tufts 70, second web 135 fails in tension under the strain produced by the formation of tufts 70, e.g., by the teeth 1100 of apparatus 1000. In general, it is believed that second web 135 should have an elongation to break of at least about 10%, at least about 30% less, at least about 50% less, or at least about 100% less than that of fibrous nonwoven web 60. Relative elongation to break values of webs used in the present invention can be measured by means known in the art, such as by standard tensile testing methods using standard tensile testing apparatuses, such as those manufactured by Instron, MTS, Thwing-Albert, and the like.

The number, spacing, and size of tufts 70 can be varied by changing the number, spacing, and size of teeth 1100 and making corresponding dimensional changes as necessary to roll 1040 and/or roll 1020. Further, the pattern of tufts 70 on the topsheet 30 and the size, shape, and location of the tuft region lateral boundaries 80 can be varied by changing the pattern of the teeth 1100 on roll 1040. That is, portions of roll 1040 may not have any teeth 1100. Similar changes can be made in roll 1020 in that portions of roll 1020 may not have any grooves 1080 and grooves 1060.

Figure 17:
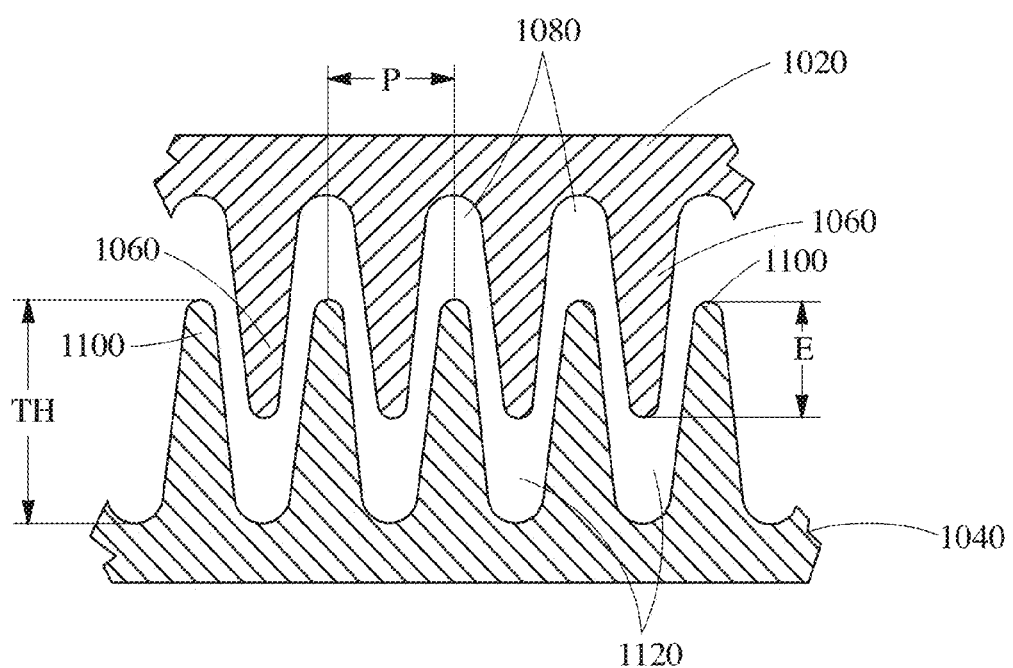
FIG. 17 is schematic of engagement of rolls.

A cross section of a portion of the intermeshing rolls 1020 and 1040 and ridges 1060 and teeth 1100 is shown in FIG. 17. As shown teeth 1100 have a tooth height TH (note that TH can also be applied to ridge height; in one embodiment tooth height and ridge height are equal), and a tooth-to-tooth spacing (or ridge-to-ridge spacing) referred to as the pitch P. As shown, depth of engagement E is a measure of the level of intermeshing of rolls 1020 and 1040 and is measured from tip of ridge 1060 to tip of tooth 1100. The depth of engagement E, tooth height TH, and pitch P can be varied as desired depending on the properties of fibrous nonwoven web 60 and second web 135, if present, and the desired characteristics of topsheet 30. For example, in general, the greater the level of engagement E, the greater the necessary elongation or fiber-to-fiber mobility characteristics the fibers of fibrous nonwoven web 60 must possess. Also, the greater the tuft area density desired, the smaller the pitch should be, and the smaller the tooth length TL and tooth distance TD should be, as described below.

Figure 18:
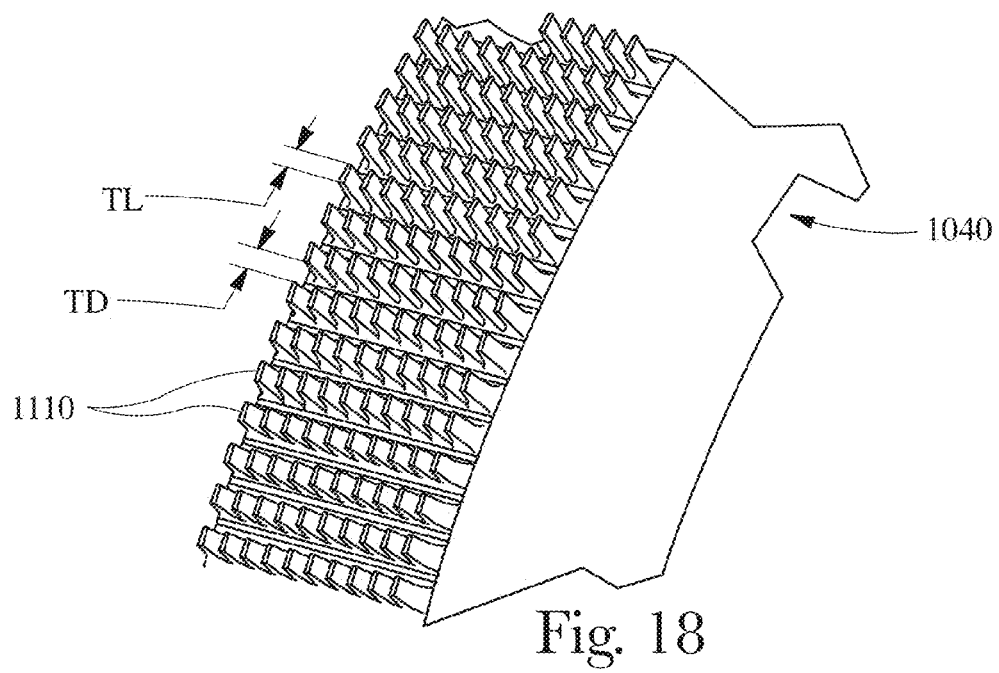
FIG. 18 is a schematic of a roll having teeth.

FIG. 18 shows one embodiment of a roll 1040 having a plurality of teeth 1100 useful for making a topsheet 30 from a fibrous nonwoven web 60 having a basis weight of between about 60 gsm and 100 gsm and a polymer film 130 (e.g., polyethylene or polypropylene).

Figure 19:
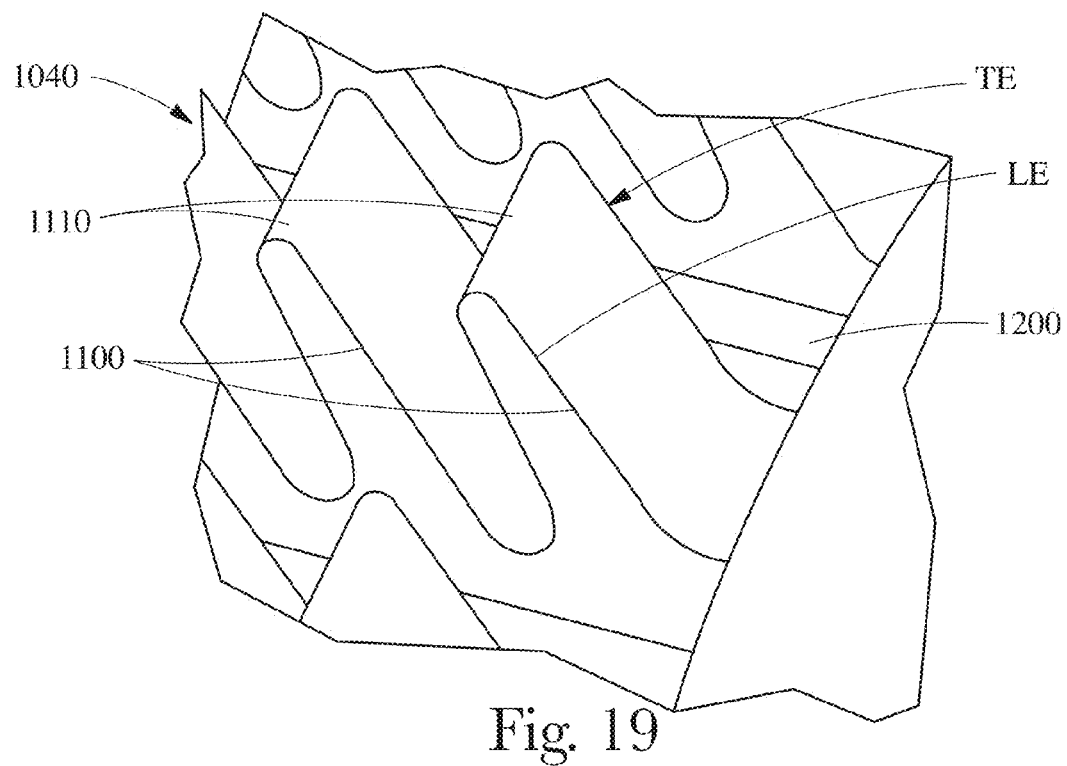
FIG. 19 is a schematic of teeth on a roll.

An enlarged view of teeth 1100 is shown in FIG. 19. In this embodiment of roll 1040, teeth 1100 have a uniform circumferential length dimension TL measured generally from the leading edge LE to the trailing edge TE at the tooth tip 1110 of about 1.25 mm and are uniformly spaced from one another circumferentially by a distance TD of about 1.5 mm. For making a topsheet 30 from a fibrous nonwoven web 60 having a total basis weight in the range of about 60 to about 100 gsm, teeth 1100 of roll 1040 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and tuft area density.

It is believed that the LE and TE should be very nearly orthogonal to the local peripheral surface 1200 of roll 1040. As well, the transition from the tip 1110 and LE or TE should be a sharp angle, such as a right angle, having a sufficiently small radius of curvature such that teeth 1100 push through fibrous nonwoven web 60 and second web 135, if present, at the LE and TE. Without being bound by theory, it is believed that having relatively sharply angled tip transitions between the tip of tooth 1100 and the LE and TE permits the teeth 1100 to punch through fibrous nonwoven web 60 or laminate 125 cleanly, that is, locally and distinctly, so that the first side 12 of fibrous nonwoven web 60 or first side 12 of laminate 125 comprises tufts 70. The characteristics of the tufts 70 can be varied as a function of line speed, as line speed affects the strain rate applied to the nonwoven fibrous web 60.

Fibrous nonwoven web 60 can be a nonwoven web in which there are minimal fiber-to-fiber bonds. For example, the precursor web can be a nonwoven web having a pattern of discrete thermal point bonds. It can be desirable to minimize the number of bond points and maximize the spacing so as to allow for maximum fiber mobility and dislocation during formation of tufts 70. In general, using fibers having relatively large diameters, and/or relatively high extension to break, and/or relatively high fiber mobility, may result in better and more distinctly formed tufts 70.

Figure 20:
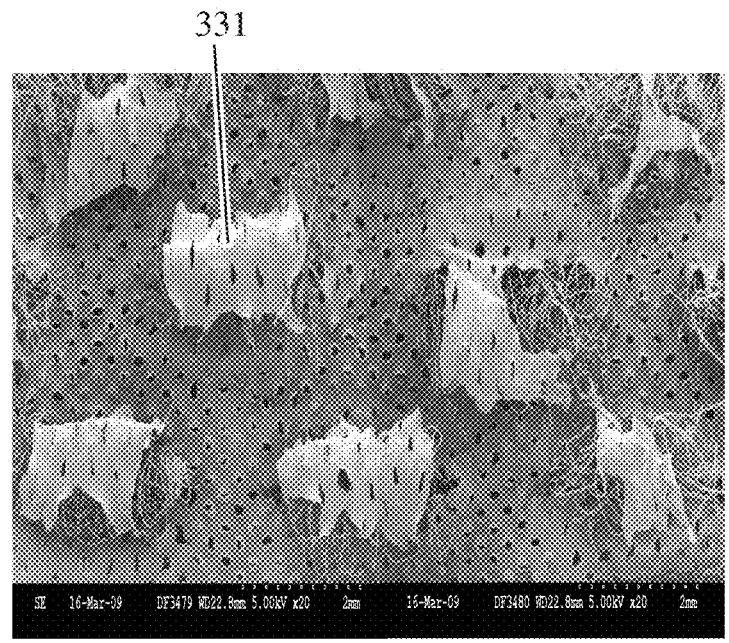
FIGS. 20-22 are scanning electron micrographs of a laminate web, the tufts having caps.

FIG. 20 is a top view scanning electron micrograph (SEM) of a laminate as disclosed herein. As shown in FIG. 12, a cap 331 covers the distal portion 231 of a particular tuft 70. In FIG. 12, the cap 331 integrally extends from at least two extension locations 254 on opposite sides of the tuft 70 and are separated by the first opening 251 and the second opening 252. When viewed from above, the cap 331 covering the distal portion 231 of a particular tuft can help obscure from view fluid, such as menses, held within the capillaries of the fibers 110 forming tuft 70. Also shown in FIG. 20 is microtexture in the polymer web, the microtexture being microapertures 172.

Figure 21:
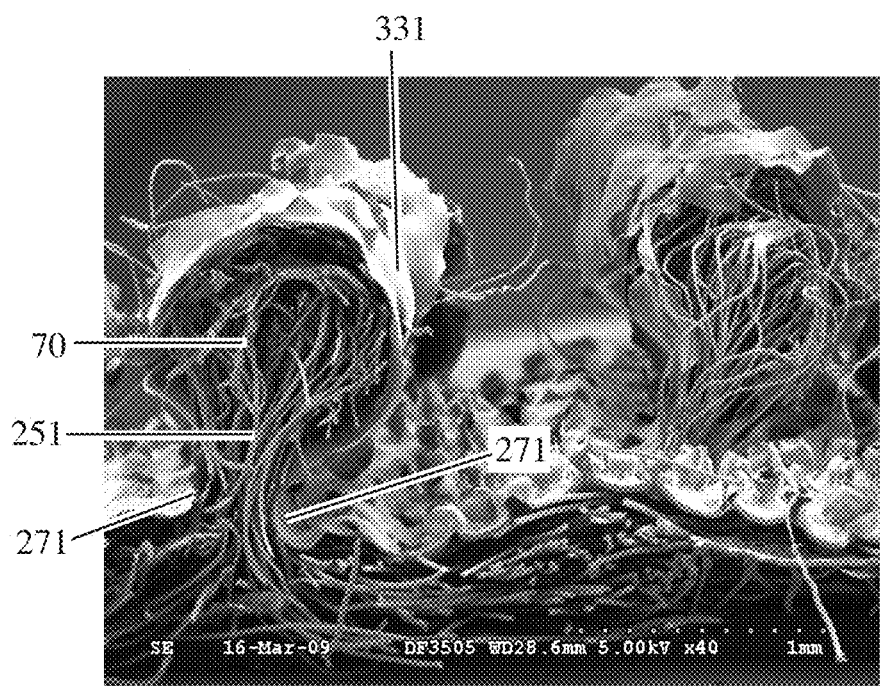

FIG. 21 is a profile view SEM of a laminate as disclosed herein. As shown in FIG. 13, cap base 271 proximal the laminate web is narrower than a portion of the cap 331 away from the cap base 271. The cap 331 in FIG. 21 is generally omega ($\Omega$) shaped.

Figure 22:
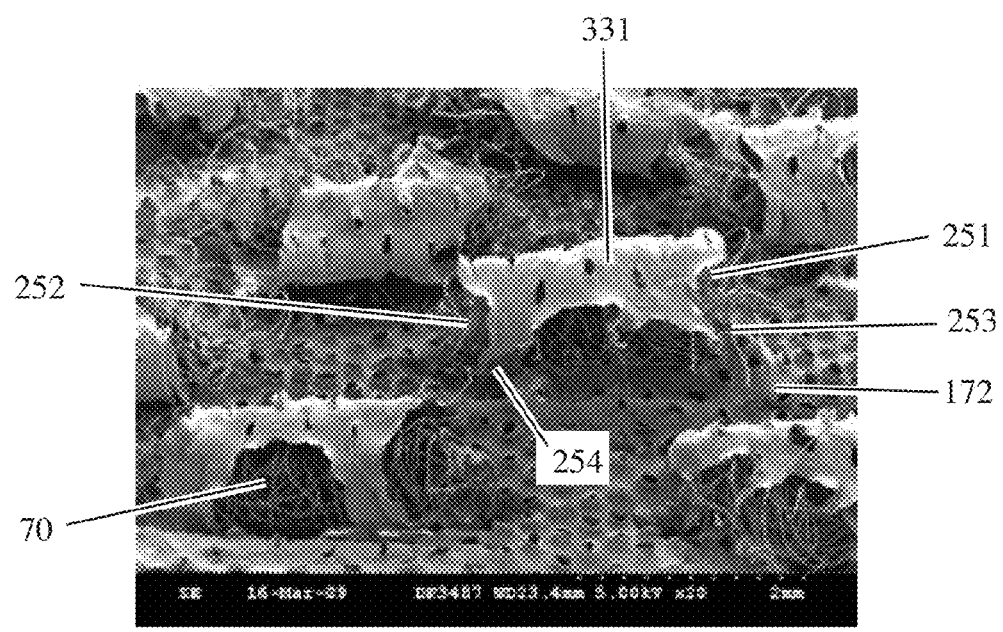

FIG. 22 is an elevated profile view SEM of a laminate as disclosed herein. As shown in FIG. 14, the cap 331 can have more than two openings such that the cap extends from the polymer film 130 at more than three discrete locations.

A laminate that could be used as a topsheet or cover wrap can be fabricated using the apparatus disclosed herein. A suitable material for nonwoven 60 can be a BBA Bico, 28 gsm, GCAS 95001796, 50/50 PE/PP, philic nonwoven, available from BBA Nonwovens. A suitable material for the polymer film 130 could be Tredegar X-33350 (philic) which is a 100 mesh precursor web, obtainable from Tredegar Corp. Two sets of process parameters listed in Table 1 could be employed to form the laminate web disclosed herein. The teeth 1110 could have a uniform circumferential length dimension TL of 0.120 inches spaced from one another circumferentially by a distance TD of 0.060 in., a pitch P of 0.060 in., a depth of engagement E of 0.114 in., a tooth height TL of 0.185 in, a radius of curvature at the tips of teeth 110 and grooves 108 of 0.005 in, and the radius of curvature in the valleys between teeth 1110 and grooves 1108 of 0.015 in. The temperature of the nonwoven in could be about 25° C. The temperature of the polymer film in could be higher than 25° C. Having the temperature of the polymer film above 25° C., for instance about 50° C., may provide for formation of acceptable caps 331. In general, it is thought that modulus of the materials processed, temperature, microtexture of the polymer film, and the web tensions on the upstream side and downstream side of the apparatus might be factors that affect the resulting structure of the laminate.

TABLE 1

|  | Elastic Modulus (N/m) | Relaxed Width (mm) | Speed (m/min) | Strain | Tension (N) |
|---|---|---|---|---|---|
| Process 1 | | | | | |
| Nonwoven In | 4043 | 165 | 367.0 | 1.021 | 13.98 |
| Polymer Film In | 1478 | 176 | 367.0 | 1.021 | 1.42 |
| Laminate Out | | 176 | 364.3 | 1.014 | 9.93 |
| Process 2 | | | | | |
| Nonwoven In | 1896 | 165 | 367.0 | 1.029 | 9.16 |
| Polymer Film In | 1478 | 176 | 367.0 | 1.021 | 1.42 |
| Laminate Out | | 176 | 364.3 | 1.02 | 7.71 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet and an absorbent core in facing relationship with said topsheet,
    said topsheet having a length, a central part, a longitudinal centerline situated along said length, a transverse centerline orthogonal to and intersecting said longitudinal centerline, and a parallel transverse axis parallel to said transverse centerline, said longitudinal centerline being dividable into thirds, one third of which is a middle third, said parallel transverse axis intersecting said middle third of said longitudinal centerline;
    wherein said topsheet comprises a fibrous nonwoven web and a first and second tuft region each of which including a plurality of tufts;
    wherein said tufts comprise fibers integral with and extending from said fibrous nonwoven web, a plurality of said fibers of said tufts being looped fibers;
    wherein said topsheet comprises a pair of tuft region lateral boundaries symmetrically disposed on opposing sides of said longitudinal centerline, each said tuft region lateral boundary separating a respective first or second tuft region from an article central portion of said topsheet that is devoid of said tufts but comprises apertures and microapertures;
    wherein said tuft region lateral boundaries are curved whereby said tuft region lateral boundaries are spaced apart from each other by a distance that is a minimum at said parallel transverse axis and gradually increases towards said longitudinally opposing ends of said tuft region lateral boundaries or are spaced apart from each other by a distance that is a maximum at said parallel transverse axis and gradually decreases towards said longitudinally opposing ends of said tuft region lateral boundaries;
    wherein said plurality of said tufts have a first color and said portion of said topsheet devoid of said tufts has a second color, wherein said first color differs from said second color by a magnitude of at least 1.1 as quantified by the CIE LAB scale.

2. An absorbent article according to claim 1, wherein said tuft region lateral boundary is between parts of said topsheet that differ in affinity to water.

3. An absorbent article according to claim 1, wherein said topsheet comprises a laminate of said fibrous nonwoven web and a polymer film, wherein said tufts extend through said polymer film.

4. An absorbent article according to claim 3, wherein said fibrous nonwoven web is relatively hydrophilic as compared to said polymer film.

5. An absorbent article according to claim 1, wherein said topsheet comprises a laminate of said fibrous nonwoven web and a polymer film, wherein each of said tufts has a tuft base proximal to said fibrous nonwoven web and a distal portion opposing said tuft base, wherein at least part of said distal portion of each of said tufts is covered by a cap, each said cap being an integral extension of said polymer film extending over said distal portion of a discrete said tuft, said cap comprising a first opening comprising a location of rupture in said polymer film above which said tuft extends.

6. An absorbent article according to claim 1, wherein said longitudinal centerline has a length, wherein each of said tuft region lateral boundaries is longer than one-fourth of said length.

7. An absorbent article according to claim 1, wherein said topsheet comprises a laminate of said fibrous nonwoven web and a second nonwoven web, wherein said tufts extend through said second nonwoven web.

8. An absorbent article according to claim 7, wherein said fibrous nonwoven web is relatively hydrophilic as compared to said second nonwoven web.

9. An absorbent article according to claim 1, wherein said absorbent core has a pair of core lateral edges spaced away from said longitudinal centerline, wherein neither of said tuft region lateral boundaries extend beyond said core lateral edges of said absorbent core.

10. An absorbent article according to claim 1, wherein said tuft region lateral boundaries are curved.

11. An absorbent article according to claim 1, wherein each said tuft region lateral boundary is between a portion of said topsheet comprising a hydrophobic lotion and said longitudinal centerline.

12. An absorbent article according to claim 1, wherein said tuft region lateral boundaries are spaced apart from each other by a distance gradually decreasing from a maximum at said parallel transverse axis to a minimum at one or both longitudinally opposing ends of said tuft region lateral boundaries.

13. An absorbent article according to claim 3, wherein said apertures and said microapertures are formed in said polymer film.

* * * * *